United States Patent
Lee et al.

(10) Patent No.: US 6,589,747 B2
(45) Date of Patent: Jul. 8, 2003

(54) METHOD FOR IDENTIFYING COMPOUNDS THAT MODULATE THE INTERACTION OF AMYLOID BETA OR ITS AGGREGATES WITH A VOLTAGE GATED SODIUM CHANNEL

(75) Inventors: Kai S. Lee, Portage, MI (US); Xiao-Dong Sun, Portage, MI (US); Bruce M. Taylor, Kalamazoo, MI (US); Dennis E. Epps, Portage, MI (US); Allen E. Buhl, Portage, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 16 days.

(21) Appl. No.: 09/742,633

(22) Filed: Dec. 21, 2000

(65) Prior Publication Data

US 2002/0004194 A1 Jan. 10, 2002

Related U.S. Application Data

(60) Provisional application No. 60/172,032, filed on Dec. 23, 1999.

(51) Int. Cl.[7] ............................ G01N 33/53; C12Q 1/00; C12N 5/08
(52) U.S. Cl. .................... 435/7.1; 435/4; 435/375; 435/368; 435/354
(58) Field of Search ....................... 435/4, 7.1, 375, 435/368, 354; 530/300, 350

(56) References Cited

U.S. PATENT DOCUMENTS

| | | |
|---|---|---|
| 5,137,873 A | 8/1992 | Yankner |
| 5,567,720 A | 10/1996 | Averback |
| 5,876,948 A | 3/1999 | Yankner |
| 5,892,018 A | 4/1999 | Welsh et al. |

FOREIGN PATENT DOCUMENTS

| | | |
|---|---|---|
| EP | WO 98/54316 | 12/1998 |
| WO | WO 94 16327 | 7/1994 |
| WO | WO 98/33815 | 8/1998 |

OTHER PUBLICATIONS

Mark et al., Brain Res., 756(1–2):205–214, 1997.*
Clausen et al., J. of Physiology, Aug. 15, 2000 527(Pt. 1):121–130.*
Arispe, et al., "Alzheimer disease amyloid beta protein forms calcium channels in bilayer membranes: blockade by tromethamine and aluminum," Proc. Natl. Acad. Sci. USA, 90, (2), 567–571 (1993).
Findeis et al., Biochemistry, 38, 6791–6800 (1999).
Furukawa et al., Nature, 379, 74–78 (1996).
Good et al., Biophysical Journal, 70, 296–304 (1996).
Goodman et al., Brain Research, 328–332 (1996).
Harper et al., Chem. Biol., 4, 119–125 (1997).
Harper et al., Chem. Biol., 4, 951–959 (1997).
Hartley et al., J. Neuroscience, 19, 8876–8884 (1999).
Kawahara et al., Biophysiol. J., 73, 67–75 (1997).
Kowall et al., Proc. Natl. Acad. Sci., 88, 7247–7251 (1991).
Lambert et al., Proc. Natl. Acad. Sci., 95, 6448–6453 (1998).
Lee et al., J. Neurosc. Methods, 2; 51–78 (1980).
Rhee et al., J. Biological Chemistry, 273, No. 22, 13379–13382 (1998).
Tollefson, Biol. Psychiatry, 27, 1133–1142 (1990).
Walsh et al., J. Biol. Chem., 272, 22364–22372 (1997).
Whitson et al., Science, 243, 1488–1490 (1989).
Yankner et al., Science, 245, 417–420 (1989).
Yankner et al., Science, 250, 279–282 (1990).
Ueda et al., J. Neurochem. vol. 68, No. 1, 265–271 (1997).
Arispe et al., Proc. Natl. Acad. Sci., 93, 1710–1715 (1996).
Bush et al, Science, 265, 1464–1467 (1994).
Chad et al, In, Cellular Neurobiology, Ed. J. Chad and H. Wheal, Oxford University Press (1991).
Colom et al., J. Neurochemistry, 70, 1925–1934 (1998).
Etcheberrigaray et al., Proc. Natl. Acad. Sci., 90, 8209–8213 (1993).

* cited by examiner

Primary Examiner—Gary Kunz
Assistant Examiner—Sharon L Turner
(74) Attorney, Agent, or Firm—Pharmacia & Upjohn; James D. Darnley, Jr.

(57) ABSTRACT

Among other things, assays and methods of diagnosis and treatment of disease (e.g., Alzheimer's disease) based on the surprising observation of an interaction between amyloid β or its aggregates with the sodium channel are provided. In particular, methods to identify compounds that modulate this interaction are provided, as well as methods of diagnosis and treatment that are based on this interaction.

3 Claims, 11 Drawing Sheets

Fig. 13

METHOD FOR IDENTIFYING COMPOUNDS THAT MODULATE THE INTERACTION OF AMYLOID BETA OR ITS AGGREGATES WITH A VOLTAGE GATED SODIUM CHANNEL

CROSS-REFERENCE TO RELATED APPLICATIONS

This application claims the benefit of provisional U.S. patent application Ser. No. 60/172,032, filed Dec. 23, 1999.

TECHNICAL FIELD OF THE INVENTION

The present invention provides, among other things, assays and methods of diagnosis and treatment that are based on the surprising observation of an interaction between amyloid β or its aggregates with sodium channels. In particular, the present invention provides methods to identify compounds that modulate this interaction, and methods of diagnosis and treatment that are based on this interaction.

BACKGROUND OF THE INVENTION

Certain neurodegenerative diseases such as Alzheimer's disease and Down's syndrome are characterized by the presence of insoluble aggregates of amyloid β (Aβ). This 39–43 amino acid peptide is derived by abnormal proteolysis from the Amyloid Precursor Protein (APP). It is well known that the amyloid β aggregates/plaques widely found in the brain and intraneuronal neurofibrillary tangles of Alzheimer's disease patients can modulate neurite outgrowth, synaptogenesis, synaptic plasticity or cause neuronal death (Mattson et al, *Trends Neurosci.*, 16, 406–415 (1993)). The mechanism(s) by which these effects are accomplished remain elusive, however (Frazer et al, *Trends Neurosci.*, 20, 67–72 (1997)).

Presently, one theory maintains that these deleterious effects may originate from amyloid β's ability to promote chronic calcium influx into neurons through modulation of neuronal calcium ion channels (Daidson et al., *Brain Res.*, 643, 324–327 (1994)), or to form transmembrane cation-permeable channels (Kawahara et al., *Biophysiol. J.*, 73, 67–75 (1997)) that indiscriminately allow calcium, sodium, and other cations to flood a cell's interior and destroy its calcium homeostasis. Calcium channel blockers such as nimodipine that can cross the blood-brain barrier have been shown to slow the progression of Alzheimer's disease in some patients (Tollefson, *Biol. Psychiatry*, 27, 1133–1142 (1990)). Similarly, zinc cation, which is known to bind at specific amyloid β 1–40 sites (Bush et al, *Science*, 265, 1464–1467 (1994)), can block the calcium influx through amyloid β 1–40 channels (Arispe et al., *Proc. Natl. Acad. Sci.*, 93, 1710–1715 (1996)).

In addition, amyloid β aggregates have been shown to induce abnormal potassium ion channel activity. In cultured hippocampal neurons, amyloid β opens a calcium-sensitive, large conductance potassium channel (i.e., iberitoxin-sensitive BK) (Furukawa et al., *Nature*, 379, 74–78 (1996)), which could lead to chronic loss of cytoplasmic potassium and destroy the ability of the neurons to generate and propagate action potentials critical for brain signaling functions. Such aberrant potassium channel activity has in fact been noted in Alzheimer's disease patients (Etchebemgaray et al., *Proc. Natl. Acad. Sci.*, 90, 8209–8213 (1993)). Likewise, in the cultured cholinergic septal cell line SN56, amyloid β (e.g., amyloid β 1–40) causes cell death by impacting a TEA-sensitive potassium channel (Colom et al., *J. Neurochemistry*, 70, 1925–1934 (1998)).

These studies suggest that amyloid β aggregates exert their effects through multiple targets. None of the targets that have been described, however, would result in the rapid and complete inhibition of neuronal electrical impulses critical for brain function that is observed with advanced stage Alzheimer's disease. Furthermore, the ion channel studies described above were performed on cultured neurons, whose properties may have been changed significantly through dedifferentiation in culture conditions. Therefore, the data currently available likely does not represent the true response of native neurons.

Recent genetic studies have shown that mutations in the amyloid protein precursor and presenilin genes affect the processing and production of amyloid β and thus are related to age of onset and susceptibility to Alzheimer's disease. Additional studies have shown that variants in ApoE genes also affect susceptibility and age of onset for Alzheimer's disease. Spontaneous Alzheimer's disease is hypothesized to be under the control of other genes and environmental factors that have yet to be identified.

Additionally, inhibition of amyloid β aggregation, and hence toxicity, is believed to be beneficial therapeutically in the treatment of Alzheimer's disease. Several reports have appeared providing evidence that small, diffusable aggregates (Lambert et al., *Proc. Natl. Acad. Sci.*, 95, 6448–6453 (1998); PCT International Application WO 98/33815), and protofibrils (Harper et al., *Chem. Biol.*, 4, 119–125 (1997); Harper et al., *Chem. Biol.*, 4, 951–959 (1997); Walsh et al., *J. Biol. Chem.*, 272, 22364–22374 (1997)), and not the completely fibrillar peptide, might be the Aβ species toxic to living cells. The physical differences in the alleged toxic species identified by these different research groups "supports the concept that different Aβ assemblies have distinct neurobiological activities, which may be manifested differently using an electrophysiological readout" (Hartley et al., *J. Neuroscience*, 19, 8876–8884 (1999)). Thus, the etiology of Alzheimer's disease may be quite complex, and may warrant a variety of different avenues of diagnosis and treatment.

Along these lines, U.S. Pat. No. 5,876,948 describes screening methods to identify inhibitors of the neurotoxic effect of amyloid β. In particular, the '948 patent purportedly provides a method of screening candidate compounds, wherein the method comprises obtaining a cell such as a primary neuron, a neuronal cell, or a cell developmentally derived from neuronal tissue. The cell is contacted with a candidate compound in the presence of a neurotoxin selected from the group consisting of amyloid β1–38, β1–40, β1–43, and β29–35, and it is determined whether the compound reduces the effect of the neurotoxin (e.g., reduces cell death), or reduces accumulation of amyloid β on the cell surface. Accordingly, this patent provides no information on how to screen for compounds that target cell events that precede cell death, apart from accumulation of the peptide on the cell surface. A need thus remains for useful assays to screen for compounds that exert protective effects at a stage prior to cell death mediated by amyloid β, and for compounds that exert their effect apart from interference with amyloid β deposition on the cell surface. Furthermore, the '948 patent does not appear to consider any effect of the aggregation state of amyloid β on neurotoxicity. A related patent, U.S. Pat. No. 5,137,873, claims a method for treating a disease that is characterized by accumulation of amyloid β, which comprises administration of a therapeutically effective amount of a tachykinin agonist such as substance P.

U.S. Pat. No. 5,892,018 pertains to DNA sequences encoding a novel subfamily of amiloride-sensitive sodium channel proteins from the human central nervous system. PCT International Application WO 98/54316 describes a new class of sodium channel protein that may function as a receptor for endogenous transmitters. Both the '018 patent and the '316 application suggest that ion channels may play some role in the pathogenesis or treatment of Alzheimer's disease (see, '316 application, pages 1 and 15; see, '018 patent, column 1, lines 50–54). However, neither document presents any assay for diagnosis of Alzheimer's disease, much less any methods for its treatment.

Thus, there remains a need for further understanding of the functioning of amyloid β or its aggregates, and means to diagnose, predict, prevent and treat diseases, disorders, and conditions that result from amyloid β or its aggregates. These and other objects and advantages of the present invention, as well as additional inventive features, will be apparent from the description of the invention provided herein.

BRIEF SUMMARY OF THE INVENTION

The present invention relates to a surprising observation of an interaction between amyloid β or its aggregates with sodium channels. Based on this novel and unexpected interaction, the present invention provides a method for identifying compounds that modulate the interaction of amyloid β or its aggregates with a sodium channel, wherein the method preferably comprises contacting a cell which comprises a sodium channel with amyloid β or its aggregates in the presence and in the absence of a test compound, and then determining whether there is any impact on the sodium channel in the presence of the test compound as compared with in the absence, with a compound that exhibits an impact being considered a modulator of the interaction of amyloid β or its aggregates with said sodium channel. In preferred embodiments, the impact on the sodium channel is assessed by either examining resting membrane potential, action potential, or measuring the fast inward sodium current. Preferably as employed in the invention, the cell is a neuronal cell, or is a non-neuronal cell, as described herein.

The method of identifying compounds that modulate the interaction of amyloid β or its aggregates with a sodium channel also can be carried out according to the invention wherein the method comprises obtaining a first cell that produces amyloid β or its aggregates, obtaining a second cell comprising a sodium channel, contacting the second cell with the first cell in the presence and absence of a test compound, and determining the activity of the sodium channel in the presence of said test compound as compared with in the absence, wherein a test compound that impacts activity is considered a modulator of the interaction of amyloid β or its aggregates with said sodium channel. Preferably one of the first and second cells is a neuronal cell and the other is a non-neuronal cell, or both of the first and second cells are either a neuronal cell or a non-neuronal cell.

Also, preferably the method of identifying compounds that modulate the interaction of amyloid β or its aggregates with a sodium channel can be carried out according to the invention wherein the method comprises the steps of obtaining a composition comprising a purified sodium channel, contacting the sodium channel with amyloid β or its aggregates in the presence and absence of a test compound, and determining the activity of the sodium channel in the presence of the test compound as compared with in the absence, wherein a test compound that impacts activity is considered a modulator of the interaction of amyloid β or its aggregates with the sodium channel.

The invention also provides a method for diagnosing Alzheimer's disease (or prion disease) in a mammal suspected of having Alzheimer's disease (or prion disease), the method comprising the step of measuring the activity of a sodium channel in a cell of the mammal, wherein reduced activity of the sodium channel is correlated with the existence of an Alzheimer's disease state (or a prion disease state).

The invention further provides a method of screening a mammal for susceptibility to Alzheimer's disease, comprising the steps of:

(a) isolating a cell from the mammal, the cell comprising a sodium channel; and (b) measuring activity of the sodium channel in the absence and in the presence of amyloid β protein;

wherein reduced activity of the sodium channel in the presence of amyloid β as compared to in the absence is correlated with a susceptibility to developing Alzheimer's disease.

Additionally, the invention provides a method for preventing, treating, or reversing diseases such as Alzheimer's disease and prion disease in a mammal, wherein the method preferably comprises contacting a sodium channel of the mammal with a compound that protects the sodium channel from a negative impact of amyloid β or its aggregates. This method optionally is carried out with use of a compound that opens the sodium channel.

Furthermore, the invention provides for the use of a compound that modulates the interaction of amyloid β or its aggregates with cellular sodium channels for the manufacture of a medicament for the treatment of a neurological disorder (e.g., Alzheimer's disease).

Additional features and variations of the invention will be apparent to those skilled in the art from the entirety of this application, including the detailed description, and all such features are intended as aspects of the invention. Likewise, features of the invention described herein can be recombined into additional embodiments that also are intended as aspects of the invention, irrespective of whether the combination of features is specifically mentioned above as an aspect or embodiment of the invention. Also, only such limitations which are described herein as critical to the invention should be viewed as such; variations of the invention lacking limitations which have not been described herein as critical are intended as aspects of the invention.

In addition to the foregoing, the invention includes, as an additional aspect, all embodiments of the invention narrower in scope in any way than the variations specifically mentioned above. Although the applicant(s) invented the full scope of the claims appended hereto, the claims appended hereto are not intended to encompass within their scope the prior art work of others. Therefore, in the event that statutory prior art within the scope of a claim is brought to the attention of the applicants by a Patent Office or other entity or individual, the applicant(s) reserve the right to exercise amendment rights under applicable patent laws to redefine the subject matter of such a claim to specifically exclude such statutory prior art or obvious variations of prior art from the scope of such a claim. Variations of the invention defined by such amended claims also are intended as aspects of the invention.

BRIEF DESCRIPTION OF THE DRAWINGS

FIG. 13 is a graph which shows the impact of amyloid β on the sodium channel (Y-axis, % decrease in $I_{Na}$) at different time points (X-axis, in minutes) of aggregation. The peak impact on activity appears at about 60–80 minutes of shake-induced aggregation of the 50 μM amyloid β 1–40. For each datapoint, the number of independent measurements from independent neurons is indicated, and error bars are provided where multiple measurements have been averaged.

Figures 1A, 1B, 1C:
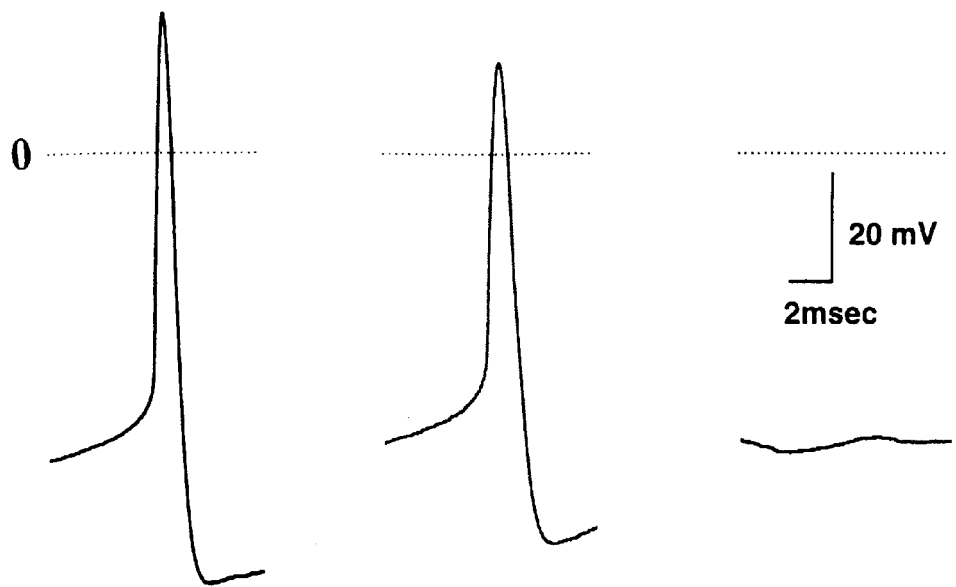
FIGS. 1A–C are recordings taken from an Axopatch 200 Amplifier which show changes of an action potential recorded from a single cortical neuron: (A) in the absence of amyloid β 1–40 peptide; (B) in the presence of 11.5 μM amyloid β1–40 peptide; or (C) following washing of the neuron with peptide-free solution.

The detailed description and examples are provided to enhance the understanding of the invention, but are not intended to limit the scope of the invention.

DETAILED DESCRIPTION OF THE INVENTION

It is well established that, in cultured cells or neonatal neurons, certain forms of amyloid β (Aβ) are neurotoxic by interfering with normal neuronal functions. However, the precise target channel(s) and subsequent changes in action potential firing patterns of native neurons in adult mammals have not been established. This important issue was examined using a highly sensitive, well-defined neuronal preparation freshly dissociated from adult rat brains and the suction pipette recording technique. It surprisingly was discovered that amyloid β depressed or eliminated neuronal action potentials by specifically blocking fast inward sodium channels, thereby shutting off neuronal impulses. Furthermore, it was determined that low molecular weight amyloid β aggregates had greater ability to deleteriously impact cell functions (i.e., including sodium channel activity) than either monomers or polymers.

Based on the foregoing, and as further described herein, the present invention provides, among other things, a method for identifying compounds that modulate the interaction of amyloid β or its aggregates with a sodium channel. Such compounds are useful in diagnosing, preventing, treating, or reversing various disorders (e.g., Alzheimer's disease and prion disease) that are characterized by disruption of sodium channels.

Amyloid β or its Aggregates

According to the invention, "amyloid β" (Aβ) is any of the sequences 1–43, 1–42, 1–41, 1–40, 1–39, and 1–38, and truncated sequences of any of the previous, resulting from β-secretase and γ-secretase cleavage of the amyloid precursor protein (see, e.g., Yan et al., *Nature,* 402, 533–537 (1999); Kang et al., *Nature,* 325, 733 (1987); Selkoe, *In, Annual Review of Neuroscience,* Cowan (Ed.), 17, ix+623, 489–517 (1994)). Aβ can be that of any species, particularly a mammalian species, and especially human. Furthermore, "amyloid β" includes any amino acid substitutions in the foregoing sequences that result in a modified peptide/protein having aggregation properties similar to the native peptide/protein. In particular, amyloid β is a protein (or peptide) comprising residues 1–38, 1–40, 1–43 or 29–35 of APP, as set forth in U.S. Pat. No. 5,876,948, and which can be produced by recombinant or synthetic means.

Amyloid β can be purchased from a variety of commercial suppliers including but not limited to Polypeptide Laboratories (Torrance, Calif., Catalog number P-0036) and Bachem Biochemica (Heidelberg, Germany). Aβ also can be produced by a cell naturally, produced by a cell using recombinant means, produced by one cell (e.g., neuronal) while its impact is assayed on another (e.g., non-neuronal), employed in its polypeptide form (i.e., either pre-aggregated or not) to contact a sodium channel, or employed as part of a composition (e.g., including micelles) to contact a sodium channel. All these various permutations, as well as additional variations that would be obvious to one skilled in the art, are encompassed by the subject invention.

"Aggregates" of amyloid β include any higher order structure formed by an association of more than one Aβ monomer with an ability to inhibit the fast inward sodium current ($I_{Na}$), and especially include a tetramer of amyloid β (i.e., a higher order structure formed by the association of four amyloid β monomers).

Aggregation of amyloid β preferably is done in an appropriate buffer. If the aggregated amyloid β subsequently is not to be used with cells, then the buffer desirably comprises about 10 mM phosphate, 100 mM NaCl, pH 7.4, or another similar buffer. If the amyloid β subsequently is to be used with cells (e.g., whole cells, isolated cells, or other), then the buffer employed for aggregation desirably comprises the same tissue culture medium in which the cells are aggregated (e.g., Hank's balanced salt solution). Aggregation desirably is carried out by shaking the mixture of amyloid β in buffer (e.g., desirably at a rate of from about 700 to 800 rpm). Optimally, aggregation is carried out for various times, particularly as described in the Examples. Desirably, aggregation is monitored, e.g., by measuring light scattering at 405 nm. More detailed information on aggregation can be obtained from the Examples, as well as the reference of Findeis et al., *Biochemistry,* 38, 6791–6800 (1999).

Furthermore, preferably prior to dissolution in the appropriate buffer, the amyloid β first preferably is treated in an appropriate fashion to obtain random coil monomer. This can be done, for instance, by treatment with hexafluoroisopropyl alcohol (HFIPA)(as described in the Examples which follow), or by acid treatment (as described in the Examples which follow, and in Findeis et al., supra).

Sodium Channels and Cells Comprising Same

The sodium channels for use in the invention include but are not limited to all native sodium channels in all tissues, especially in the nervous system, and most particularly in cells from the brain and spinal cord tissues, which are targets for Aβ of various forms and at various stages of aggregation (i.e., which are sensitive at some level to the deleterious effects of Aβ or its aggregates). Thus, according to the invention, a "cell" preferably is a primary neuron, a neuronal cell, or a cell that is developmentally derived from neuronal tissue.

The invention also desirably can be carried out with the use of sodium channels in cells from non-neuronal tissue (i.e., non-neuronal cells). A "non-neuronal cell" is a cell that is not a primary neuron, a neuronal cell, or a cell that is developmentally derived from neuronal tissue. Preferred non-neuronal cells for use in the invention include but are not limited to primary cells that have a cell geometry, cell number, and degree of homogeneity that allows relatively easy harvesting of the cells for single-cell electrophysiology assays. Especially preferred non-neuronal cells are muscle cells, especially muscle cells confirmed to have a sodium channel similar in function to that of neuronal cells (e.g., skeletal muscle cells, and cardiac muscle cells such as pacemaker cells, atrial cells, atrial-ventricular nodal cells, left ventricular cells, right ventricular cells, papillary muscle cells, and Purkinje fiber cells), although other muscle cells that have not been so characterized also can be employed (e.g., smooth muscle cells, particularly cardiac smooth muscle cells). Cells that are less than optimal for electrophysiology studies (e.g., those having a smaller size or a flat versus rounded morphology, those having a low cell number, and/or those which are located as part of a nonhomogeneous tissue) also can be used, with appropriate optimization of the assays according to the invention. Such cells include blood cells, kidney cells, and epithelial cells (i.e., those lining the intestines). None of these cells are developmentally derived from neuronal cells. Additionally, cultured cells including non-neuronal cancer cell lines also optionally can be employed, so long as the cells can be maintained under conditions that de-differentiation is infrequent and unlikely. Such established cell lines differ from primary cells in that the cell lines have undergone a genetic change that renders them effectively immortal.

Preferably the cell is an avian cell, or a mammalian cell including but not limited to that of a rodent, primate (e.g., monkey, ape, gorilla, chimpanzee, gibbon, orangutan, and the like), feline, canine, ungulate (e.g., ruminant or swine), and particularly that of a human. Desirably the cell is of a mammalian (especially a human) species. A cell can be present as a single entity, or can be part of a larger collection of cells, such as, for instance, a cell culture, a tissue (e.g., neural tissue), an organ (e.g., brain or spinal cord), an organ system (e.g., central nervous system), or an organism (e.g., mammal).

Preferably a "sodium channel" is a fast inward sodium channel. A "fast inward sodium channel" is a large transmembrane, voltage-sensitive protein that opens (i.e., provides a passage through the cell membrane, from a cell's exterior to its interior) in response to membrane depolarization. Once opened, the channel allows massive influx of sodium ion into the cell, for a few milliseconds only, and in a neuronal cell, allows the generation of the action potential that is critical for conducting nerve impulses. Without opening of fast inward sodium channels, a neuronal network stays silent and becomes non-functional. The sodium channels that are contemplated for use in the invention include those known in the art as "voltage-gated", "non-voltage-gated", and "exchangers". The current measured at a fast inward sodium channel is the fast inward sodium current.

All tetrodotoxin (TTX)-sensitive and TTX-insensitive sodium channels from tissue/cell sources stated above are the key targets for amyloid β of various forms and at various stages of aggregation. However, in preferred embodiments, the invention is practiced using sodium channels that are TTX-sensitive.

The sodium channels useful for practice of the invention further include non-native sodium channels (e.g., those obtained by recombinant means, such as molecularly cloned sodium channels, including those cloned from cells of any tissues, particularly from the central nervous system, and especially from brain) as targets for amyloid β of various forms and at various stages of aggregation. Non-native sodium channels useful for conducting assays of the invention are sensitive at some level to the deleterious effects of amyloid β or its aggregates. However, non-native sodium channels that are not sensitive to the deleterious effects of amyloid β or its aggregates are useful for determining those regions at which amyloid β interacts with the channel (e.g., by comparing the structure of the non-native channel with that of the native channel). Such non-native sodium channels include but are not limited to those described in U.S. Pat. No. 5,892,018, and PCT International Application WO 98/54316.

Thus, the deleterious activity of amyloid β or its aggregates can be studied and modulated by introducing into cells expression vectors that result in production of high levels of a sodium channel. Along these lines, the invention further provides methods of using purified sodium channels (or portions thereof) and genetically engineered host cells that express recombinant sodium channels to evaluate and screen for modulators of the interaction between amyloid β peptide and the sodium channel.

Assay for Modulators of the Interaction of Amyloid β or its Aggregates with the Sodium Channel The present invention provides methods of screening for putative modulators using any of a variety of drug screening techniques. Such modulators will provide the basis for pharmaceutical compositions for the treatment and amelioration of symptoms associated with the activity of amyloid β or its aggregates.

Modulators of the interaction of amyloid β or its aggregates with the sodium channel include modulators that facilitate (i.e., increase the effectiveness of, or make happen more readily) the interaction of amyloid β or its aggregates with the sodium channel, and compounds that impair (i.e., decrease the effectiveness of, or make happen less readily) the interaction of amyloid β or its aggregates with the sodium channel. In the context of the present invention, compounds that impair the interaction of amyloid β or its aggregates with the sodium channel may find particular use in the prevention and/or treatment of Alzheimer's disease and prion disease, as well as other disorders, as further described herein.

According to the invention, modulators that impair the interaction of amyloid β or its aggregates with the sodium channel allow a reduction of no more than from 0% to about 20% in the fast inward sodium current when a sodium channel is contacted with amyloid β or its aggregates and the modulator (i.e., as compared to when a sodium channel is contacted with amyloid β or its aggregates in the absence of the modulator), or cause the reduction that occurs following such contacting to have a delayed onset and/or less prolonged duration (i.e., as compared to when a sodium channel is contacted with amyloid β or its aggregates in the absence of the modulator).

By comparison, modulators that facilitate the interaction of amyloid β or its aggregates with the sodium channel increase the reduction in the fast inward sodium current when a sodium channel is exposed to amyloid β or its aggregates by at least from about 10% to about 20% (i.e., as compared to when a sodium channel is exposed to amyloid β or its aggregates in the absence of the modulator), or cause the reduction that occurs following such exposure to have a more rapid onset and/or more prolonged duration (i.e., as compared to when a sodium channel is contacted with amyloid β or its aggregates in the absence of the modulator).

In one embodiment, the invention provides a method for identifying compounds that modulate the interaction of amyloid β or its aggregates with a sodium channel preferably comprising:

(a) obtaining a cell that comprises a sodium channel;

(b) contacting the sodium channel with amyloid β or its aggregates in the presence and absence of a test compound; and (c) determining the activity of the sodium channel in the presence of the test compound as compared with in the absence, wherein a test compound that impacts activity is considered a modulator of the interaction of amyloid β or its aggregates with the sodium channel.

The sodium channels employed in the assay methods of the invention may be free in solution, affixed to a solid support, present on a cell surface, or located in micelles or other structures. Additionally, as discussed above, the sodium channel (and/or amyloid β or its aggregates) can be provided to a cell by recombinant means (e.g., produced within the cell by virtue of recombinant DNA modifications of the cell, or produced by a neighboring cell such as a neuronal cell and employed to impact a non-neuronal cell being studied). The amyloid β as applied for contacting the sodium channel optionally is in polypeptide form, and, as so supplied, can be either pre-aggregated for various lengths of time (e.g., as previously described and as set out in the Examples which follow), or can be employed for contacting in its monomer form.

In one variation, the method preferably can be carried out by:

(a) obtaining a first cell that produces amyloid β or its aggregates;

(b) obtaining a second cell comprising a sodium channel;

(c) contacting the second cell with the first cell in the presence and absence of a test compound; and (d) determining the activity of the sodium channel in the presence of the test compound as compared with in the absence, wherein a test compound that impacts activity is considered a modulator of the interaction of amyloid β or its aggregates with the sodium channel. The method preferably can be carried out wherein the first and second cell are of the same type cells, thus both the first and second cells are either a neuronal cell or a non-neuronal cell (e.g., both are either neuronal or non-neuronal cells, or both are of the same type of either neuronal or non-neuronal cells). The method also preferably can be carried out wherein the first and the second cells are different types of cells, for instance, one of the first and second cells is a neuronal cell and the other is a non-neuronal cell, or one is of one type of a neuronal or non-neuronal cell and the other is of another type of neuronal or non-neuronal cell).

The method also optionally can be carried out by:

(a) obtaining a composition comprising a purified sodium channel;

(b) contacting the sodium channel with amyloid β or its aggregates in the presence and absence of a test compound; and (c) determining the activity of the sodium channel in the presence of the test compound as compared with in the absence, wherein a test compound that impacts activity is considered a modulator of the interaction of amyloid β or its aggregates with the sodium channel.

The assay methods described herein preferably are carried out wherein the activity of the sodium channel (and hence the impact on the sodium channel) in the presence of the test compound as compared with in the absence is determined or assessed by a method selected from the group consisting of examining resting membrane potential, examining action potential, or measuring the fast inward sodium current. In comparison to the fast inward sodium current, there are slow inward sodium currents, but these play a minimal role in the generation of action potentials. In particular, reduction and/or abrogration of action potential can be assessed, as well as the relief of such reduction or blockage (e.g., by so-called "sodium channel openers", as described below). Likewise, reduction or blockage of the fast inward sodium current can be assessed, as well as the relief of such reduction or blockage (e.g., by so-called sodium channel "openers"). Such measurements can be done using methods known in the art, and described in the Examples that follow.

The modulation of the effects of amyloid β or its aggregates on a sodium channel by an agent being tested (i.e., a "test compound") may be measured by means described herein, or other means known in the art, which are amenable to biochemical or cell-based high throughput screening (HTS) assays (e.g., melanophore assay systems to investigate receptor-ligand interactions, yeast-based assay systems, and potentially mammalian cell expression systems, and the like). For a review, see Jayawickreme and Kost, *Curr. Opin. Biotechnol.*,8, 629–634 (1997). Automated and miniaturized HTS assays are also comprehended as described, for example, in Houston and Banks, *Curr. Opin. Biotechnol.*, 8, 734–740 (1997).

Such HTS assays are used to screen libraries of compounds to identify particular compounds that exhibit a desired ability to modulate the interaction of amyloid β or its aggregates with the sodium channel. Any library of compounds may be used, including chemical libraries, natural product libraries, combinatorial libraries comprising random or designed oligopeptides, oligonucleotides, or other organic compounds.

Chemical libraries may contain known compounds, proprietary structural analogs of known compounds, or compounds that are identified from natural product screening.

Natural product libraries are collections of materials isolated from natural sources, typically, microorganisms, animals, plants, or marine organisms. Natural products are isolated from their sources by fermentation of microorganisms followed by isolation and extraction of the fermentation broths or by direct extraction from the microorganisms or tissues (plants or animal) themselves. Natural product libraries include polyketides, non-ribosomal peptides, and variants (including non-naturally occurring variants) thereof. For a review, see Cane et al., *Science,* 282, 63–68 (1998).

Combinatorial libraries are composed of large numbers of related compounds, such as peptides, oligonucleotides, or other organic compounds as a mixture. Such compounds are relatively straightforward to design and prepare by traditional automated synthesis protocols, PCR, cloning or proprietary synthetic methods. Of particular interest are peptide and oligonucleotide combinatorial libraries.

Still other libraries of interest include peptide, protein, peptidomimetic, multiparallel synthetic collection, recombinatorial, and polypeptide libraries. For a review of combinatorial chemistry and libraries created thereby, see Myers, *Curr. Opin. Biotechnol.,* 8, 701–707 (1997).

Once compounds have been identified that show activity as modulators of the interaction of amyloid β or its aggregates with the sodium channel, a program of optimization can be undertaken in an effort to improve the potency and or selectivity of the activity, if so desired. This analysis of structure-activity relationships (SAR) typically involves an iterative series of selective modifications of compound structures and their correlation to biochemical or biological activity. Families of related compounds can be designed that all exhibit the desired activity, with certain members of the family potentially qualifying as therapeutic candidates.

Accordingly, the invention provides for the use of a compound that modulates the interaction of amyloid β or its aggregates with sodium channels for the manufacture of a medicament for the treatment of a neurological disorder (e.g., Alzheimer's disease). In particular, the present provides compounds that protect sodium channels from the inhibitory action of amyloid β of various forms and at various stages of aggregation.

The present invention further provides compounds that open sodium channels in the presence of amyloid β of various forms and at various stages of aggregation. Such compounds ("sodium channel openers") can be employed to impact all action potentials generated by sodium channels, as viable targets for amyloid β of various forms and at various stages of aggregation. Desirably according to the invention, a sodium channel opener also can be a compound that opens sodium channels in the absence of amyloid β of various forms and at various stages of aggregation. Examples of sodium channel openers include but are not limited to veratridine and DP1201. Veratridine and DP1201, however, change the gating mechanism of the channel allowing too much sodium in the cell, and thus while useful in a research context, may not prove as useful in the treatment of disease.

Similarly, these and other compounds according to the invention can be employed to impact all calcium and/or potassium channels as viable targets for amyloid β of various forms and at various stages of aggregation. In particular, preferably according to the invention, a modulator identified according to the methods described herein can be employed to treat Alzheimer's disease (or prion disease) as part of a composition comprising the modulator. The present invention desirably provides a compound identified as a modulator according to the screening methods described herein. The invention further preferably provides a composition comprising such a compound so identified in a pharmaceutically acceptable carrier. Furthermore, the invention preferably provides a method of using a compound so identified in the manufacture of a medicament for the prevention, treatment, or reversal of Alzheimer's disease (or prior disease) in a mammal.

Host Cell Expression Systems

As previously indicated, both the sodium channel (or constituent components thereof) and/or amyloid β can be provided to cells in the form of their encoding nucleic acids, and thus produced by the neuronal cell, or can be introduced into a host cell in their polypeptide form. The term "polypeptide" as used herein shall include all peptides (e.g., portions of proteins) and proteins (i.e., having an amino and carboxyl terminus) whether recombinant, synthetic, or purified from natural sources.

Accordingly, host cells are provided, including prokaryotic or eukaryotic cells, either stably or transiently modified by introduction of a polynucleotide to permit expression of the encoded sodium channel (or constituent components thereof) and/or amyloid β, or stably or transiently modified by introduction of the sodium channel itself (or constituent components thereof) and/or amyloid β. While eukaryotic cells such as neuronal cells can be applied directly in the assays of the invention, other eukaryotic cells or prokaryotic cells may prove useful in other ways (e.g., for in vitro protein production, or for construction of other expression vectors appropriate for use in neuronal cells).

The form in which polynucleotides that encode the sodium channel (or constituent components thereof) and/or amyloid β, and the sodium channel itself (or constituent components thereof) and/or amyloid β are introduced into cells can be further described as a "construct". A "construct" is any form of molecule in which a polypeptide sequence (e.g., sodium channel or constituent components thereof and/or amyloid β) or its encoding polynucleotide sequence is joined to or forms part of a larger molecule. The connection between the polynucleotide and/or polypeptide sequence and its site of attachment in the molecule preferably can be by a noncovalent bond (e.g., as in antibody/antigen binding), or by a covalent bond.

Along these lines, a "construct" includes, but is not limited to a vector (e.g., having genetic incorporation of a polypeptide coding sequence into a polynucleotide vector), or a conjugate-type vector (e.g., wherein a coding sequence, polypeptide sequence, or other moiety is noncovalently associated with a vector), or other appropriate moiety that can be employed for effecting cell entry. As used herein a "vector" is a vehicle capable of effecting entry into a cell, e.g., particularly for gene transfer, and has the general meaning of that term as understood by those of skill in the art.

The invention accordingly contemplates expression constructs comprising polynucleotides that encode the sodium channel (or constituent components thereof) and/or amyloid β operatively linked to an endogenous or exogenous expression control DNA sequence and a transcription terminator. Expression control DNA sequences include promoters, enhancers, and operators, and are generally selected based on the expression systems in which the expression construct is to be used. Preferred promoter and enhancer sequences are generally selected for the ability to increase gene expression, while operator sequences are generally selected for the ability to regulate gene expression. Preferred constructs of the invention also include sequences necessary for replication in a host cell. Expression constructs are preferably used for production of an encoded sodium channel (or constituent components thereof) and/or amyloid β.

Thus, polynucleotides of the invention may be introduced into the host cell desirably as part of a circular plasmid, or as linear DNA comprising an isolated protein coding region, contained on a viral vector, or by any other appropriate means. Methods for introducing DNA in to a host cell include transformation, transfection, electroporation, nuclear injection, or fusion with carriers such as liposomes, micelles, ghost cells, and protoplasts, to name but a few.

Any appropriate expression vector (e.g., as described in Pouwels et al., *Cloning Vectors: A Laboratory Manual (Elsevier, N.Y.:* 1985)) and corresponding suitable host can be employed for production of polypeptides/proteins for practice of the invention. Expression hosts include, but are not limited to, bacteria, yeast, fungal, mammalian, plant, and insect host cell systems including baculovirus systems (e.g., as described by Luckow et al., *Bio/Technology,* 6, 47 (1988)) to name but a few, and established cell lines such as the COS-7, C127, 3T3, CHO, HeLa, BHK cell line, and the like.

For introduction into cells, use of a construct that is capable of entering that particular type of cell is preferred (e.g., a herpes virus vector for entry into a neuronal cell). Other viral vectors include, but are not limited to, expression vectors derived from retroviruses, adenovirus, or vaccinia virus. Alternately, the proteins can be delivered to target cells in liposomes.

Similarly, in the different hosts, the nature of the non-coding DNA upstream of the coding region of the sodium channel (or constituent components thereof) and/or amyloid β polynucleotide sequences should be composed of transcription/translation signals appropriate for the host.

Host cells of the invention are useful in methods for large-scale production or use of sodium channel (or constituent components thereof) and/or amyloid β polypeptides. For example, recombinant sodium channel (or constituent components thereof) and/or amyloid β products can be produced and isolated from host cells for use in in vitro assays such as drug screening assays. In such methods, the host cells are grown in a suitable culture medium and the desired polypeptide product is isolated from the cells or from the medium in which the cells are grown.

The polypeptide product (e.g., sodium channel or Aβ) optionally can be isolated by purification methods known in the art, such as conventional chromatographic methods including immunoaffinity chromatography, receptor affinity chromatography, hydrophobic interaction chromatography, lectin affinity chromatography, size exclusion filtration, cation or anion exchange chromatography, high performance liquid chromatography (HPLC), reverse-phase HPLC, and the like.

Still other methods of purification include those in which the desired protein is expressed and purified as a fusion protein in which the sodium channel (or constituent components thereof) and/or amyloid β is ligated to a heterologous amino acid sequence. Suitable heterologous sequences can include a specific tag, label, or chelating moiety that is recognized by a specific binding partner or agent. For example, for screening of peptide libraries for modulators of the interaction between the sodium channel and amyloid β, it is possible to produce either component fused to a selected heterologous protein selected to be specifically identifiable, e.g., using a probe antibody. A fusion protein also may be engineered to contain a cleavage site (e.g., a factor XA or enterokinase sensitive sequence) located between the sodium channel (or constituent components thereof) and/or amyloid β sequence and the heterologous protein sequence, to permit the sodium channel (or constituent components thereof) and/or amyloid β to be cleaved from the heterologous protein and subsequently purified. Cleavage of the fusion component may produce a form of the desired protein having additional amino acid residues resulting from the cleavage process.

In a preferred embodiment of the present invention, a sodium channel (or constituent components thereof) and/or amyloid β, or a host cell that expresses coding sequences for a sodium channel (or constituent components thereof) and/or amyloid β may be used to screen for peptides, or other molecules, such as organic or inorganic molecules, that act as modulators of the interaction between the sodium channel (or constituent components thereof) and amyloid β. For example, screening of peptide libraries or organic libraries made by combinatorial chemistry with the aforementioned polypeptides or cell lines may be useful for identification of therapeutic molecules that function by modulating the interaction between a sodium channel and amyloid β. Synthetic compounds, natural products, and other sources of potentially biologically active materials can be screened in a number of ways deemed routine by those of skill in the art.

Contacting

The "contacting" described above between amyloid β or its aggregates with a sodium channel, and optionally, with a modulator according to the invention can be done by any means known to those skilled in the art, and described herein, by which the apparent touching or mutual tangency of amyloid β or its aggregates with a sodium channel, and optionally, with a modulator according to the invention, can be effected. For instance, contacting can be done by mixing these components in a small volume of the same solution. Alternately, the components need not necessarily be brought into contact in a small volume, as, for instance, in cases where the one or more of the components is present in, and/or is administered to, a host, and travels within the host by the bloodstream, cerebrospinal fluid, or other bodily fluid. Also, the components need not always be added all at the same time; it suffices that all the components necessary for the assay just are present together at some time during the assay (or treatment, as described further below).

The method of the present invention can be employed for means of contact either in vitro or in vivo, for instance for research, diagnosis, or therapy. According to the invention "contacting" comprises any means of contact; the method is not dependent on any particular means and is not to be so construed. Such means are well known to those skilled in the art, and also are exemplified herein.

However, for components provided in the form of a construct (e.g., polynucleotide forms of sodium channel proteins and amyloid β), contacting can be effected for instance, either in vitro (e.g., in tissue culture studies) or in vivo by electroporation, transformation, transduction, conjugation or triparental mating, (co)transfection, (co-) infection, membrane fusion with cationic lipids, high velocity bombardment with DNA-coated microprojectiles, incubation with calcium phosphate-DNA precipitate, direct microinjection into single cells, and the like. Similarly, the constructs can be introduced by means of cationic lipids, e.g., liposomes. Such liposomes are commercially available (e.g., Lipofectin®, Lipofectamine™, and the like, supplied by Life Technologies, Gibco BRL, Gaithersburg, Md., and other commercial vendors). Other methods also are available and are known to those skilled in the art.

Diagnostic and Therapeutic Methods

The compounds uncovered according to the invention that modulate the interaction of amyloid β or its aggregates with the sodium channel potentially can be employed in the diagnosis, prevention, treatment, or reversal of disorders that are due to deleterious effects of amyloid β within the central nervous system, i.e., mediated by the effect of Aβ on the sodium channel.

"Prevention" as used herein refers to preventing a disorder from occurring in a mammal (especially a human) that may be predisposed to the disorder, but has not yet been diagnosed as having it. "Treating" means: inhibiting the disorder, i.e., arresting its development; relieving the disorder, i.e., causing its regression; or ameliorating the disorder, i.e., reducing the severity of symptoms associated with the disorder. "Disorder" is intended to encompass medical disorders, diseases, conditions, syndromes, and the like, without limitation.

In particular, the method of the invention may be employed to treat mammals (i.e., especially humans) therapeutically or prophylactically, for instance, mammals that are or may be subject to disorders that include but are not limited to Alzheimer's disease, adult Down's syndrome (i.e., over the age of 40 years), hereditary cerebral hemorrhage with amyloidosis, non-inherited congophilic angiopathy with cerebral hemorrhage, and senile dementia. These are all disorders that are characterized by the presence of Aβ, for instance, deposited in aggregates/plaques. It is demonstrated for the first time herein that Aβ deleteriously impacts sodium channel functioning. Such an impact on sodium channel functioning could produce the neural and cognitive defects and other symptoms that are observed with these disorders. Thus, it is reasonable to expect that modulators that impair the ability of Aβ to deleteriously impact sodium channel functioning can be employed to reduce, if not entirely prevent, the neural and cognitive defects and other symptoms that are observed with these disorders.

Accordingly, the present invention provides a method for diagnosing Alzheimer's disease in a mammal (e.g., a human) suspected of having Alzheimer's disease, the method comprising the step of measuring the activity of a sodium channel in a neuronal cell of the mammal, wherein reduced activity of the sodium channel is correlated with the existence of an Alzheimer's disease state. Desirably the activity is determined by a method selected from the group consisting of examining resting membrane potential, examining action potential, and measuring the fast inward sodium current. It is expected that the methods of the invention will prove useful in such diagnosis or prediction since it is anticipated that an impact on the sodium ion channel can occur prior to manifestation of all the symptoms of the disorder (e.g., prior to all the symptoms of Alzheimer's disease). If the functionality of the sodium channel appears to be reduced, optionally further tests can be carried out to confirm that the reduced functioning is due to an impact of amyloid β or its aggregates on the sodium channel. For instance, the method further optionally can comprise a step of measuring the amount of amyloid β or its aggregates in the cell (e.g., wherein the cell is a neuronal cell that has been isolated from the mammal), on the surface of the cell, or in extracellular fluid from the mammal that contacts the cell, wherein the presence of amyloid β or its aggregates in the cell or fluid (e.g., along with the presence of reduced sodium channel activity) is correlated with the existence of an Alzheimer's disease state. Preferably according to the invention, the fluid tested is cerebrospinal fluid.

The invention further provides a method of screening a mammal for susceptibility to Alzheimer's disease, comprising the steps of:

(a) isolating a cell from the mammal, the cell comprising a sodium channel; and (b) measuring activity of the sodium channel in the absence and in the presence of amyloid β protein or its aggregates;

wherein reduced activity of the sodium channel in the presence of amyloid β or its aggregates as compared to in the absence is correlated with a susceptibility to developing Alzheimer's disease.

The present invention also provides a method for preventing, treating, or reversing Alzheimer's disease in a mammal, the method preferably comprising contacting a sodium channel of the mammal with a compound that protects the sodium channel from a reduction in sodium channel activity due to amyloid β or its aggregates. Treatment with compounds identified according to the screening methods of the invention is explicitly contemplated.

Also, like Alzheimer's disease, prion disease is a neurodegenerative disease in which prion protein causes neurotoxicity. Those knowledgeable in the art would understand that prion protein, like amyloid β or its aggregates, can affect neural sodium channel function as part of the pathology of prion disease. In like manner, the sodium channel impact of prion proteins can be useful in finding new therapies for prion disease. For instance, certain of the modulators identified as useful for Alzheimer's disease may be expected to have beneficial effects in prion disease by virtue of restoring or alleviating a block on sodium channel functioning. Analysis of sodium channel proteins and sodium channel regulatory proteins will provide the basis for diagnostic tests of Alzheimer's disease and clinical markers for following progression and the efficacy of prion therapy.

The invention accordingly further provides method for diagnosing prion disease in a mammal suspected of having prion disease, the method comprising the step of measuring the activity of a sodium channel in a cell of the mammal, wherein reduced activity of the sodium channel is correlated with the existence of a prion disease state.

Similarly, the present invention provides a method for preventing, treating, or reversing prion disease in a mammal, the method desirably comprising contacting a sodium channel of the mammal with a compound that protects the sodium channel from a reduction in sodium channel activity due to amyloid β or its aggregates.

In a preferred embodiment, the present invention provides compounds that are capable of opening the sodium channel, i.e., "sodium channel openers". Accordingly, the present invention provides a method for preventing, treating, or reversing Alzheimer's disease in a mammal, wherein the method desirably comprises contacting a sodium channel of the mammal with a compound that opens the sodium channel.

Also, the invention provides a method for preventing, treating, or reversing prion disease in a mammal, wherein the method preferably comprises contacting a sodium channel of the mammal with a compound that opens the sodium channel.

In terms of therapeutic uses, various assays will be employed to evaluate the efficacy of a particular therapeutic treatment regimen, and to determine a normal or standard profile. Such assays include the specific sodium ion channel studies set out in the Examples that follow. Such assays may be tailored to suit a particular application, and may be used in animal studies, in clinical trials, or in monitoring the treatment of an individual patient.

To provide a basis for the diagnosis and treatment of disease, a normal or standard profile must be established. This is accomplished by combining a biological sample taken from a normal subject. Standard values obtained from normal samples may be compared with values obtained from samples from subjects potentially affected by a disorder or disease related to the deleterious effects of Aβ or its aggregates. Deviation between standard and subject values establishes the presence of the disease state. If disease is established, a therapeutic agent is administered, if so desired, and treatment profile or values may be generated. The assay may be repeated on a regular basis to evaluate whether the values progress toward or return to the normal or standard pattern. Successive treatment profiles may be used to show the efficacy of treatment over a period of several days or several months.

Other Uses

Apart from the diagnostic and therapeutic uses described above, there are many additional uses and discoveries that stem from the present invention.

For instance, the discovery described herein of sodium channels as a novel mechanism of negative impact for Aβ indicates that sodium channels are one of previously unknown elements linked to Alzheimer's susceptibility. Thus, sodium channel genes or genes for regulators of the sodium channel impacted by Aβ activity may be associated with susceptibility for Alzheimer's disease. Analysis of genetic variants of both the structural genes sodium channel and sodium channel regulatory proteins can be used for linkage of specific mutants or variants of these genes with susceptibility to Alzheimer's disease. Tests for these mutant or variant genes will be diagnostic for Alzheimer's disease and susceptibility to this disease. Thus, the discovery as described herein of the link between sodium channels and the deleterious actions of Aβ and its aggregates will provide the basis for both diagnostic tests for Alzheimer's disease and clinical markers for following the progression and efficacy of treatments for Alzheimer's disease.

Additionally, the present invention also provides for the use of kinetic measurements of Aβ peptide effects (as described in Example 5) in conjunction with measurements of the inward sodium current. Such a kinetic approach similarly can be employed to discover drugs used to treat Alzheimer's disease.

Pharmaceutical Compositions

The present invention thus further provides pharmaceutical compositions. Pharmaceutical compositions optionally comprise as an active agent modulators (as previously described), or polynucleotides that encode a sodium channel (or a peptide thereof) and/or amyloid β, along with a biocompatible pharmaceutical carrier, adjuvant, or vehicle. Preferably, the active agent is active in treating a medical condition that is due to the negative effects of amyloid β or its aggregates. The composition can include the agent as the only active moiety or in combination with other active agents, optionally mixed with excipient(s) or other pharmaceutically acceptable carriers.

Pharmaceutically acceptable excipients to be added to pharmaceutical compositions are well-known to those who are skilled in the art, and are readily available. The choice of excipient will be determined in part by the particular method used to administer the composition according to the invention. Accordingly, there is a wide variety of suitable formulations for use in the context of the present invention. The following methods and excipients are merely exemplary and are in no way limiting.

Techniques for formulation and administration of pharmaceutical compositions may be found in *Remington's Pharmaceutical Sciences,* 18th Ed., Mack Publishing Co, Easton Pa., 1990, and are well known to those skilled in the art. The pharmaceutical compositions of the present invention may be manufactured using any conventional method, e.g., mixing, dissolving, granulating, dragee-making, levigating, emulsifying, encapsulating, entrapping, melt-spinning, spray-drying, or lyophilizing processes. However, the optimal pharmaceutical formulation will be determined by one of skill in the art depending on the route of administration and the desired dosage. Such formulations may influence the physical state, stability, rate of in vivo release, and rate of in vivo clearance of the administered agent.

Depending on the condition being treated, these pharmaceutical compositions may be formulated and administered systemically or locally.

The pharmaceutical compositions may be administered to the subject by any conventional method, including parenteral and enteral techniques. Parenteral administration modalities include those in which the composition is administered by a route other than through the gastrointestinal tract, for example, intravenous, intraarterial, intraperitoneal, intramedullary, intramuscular, intraarticular, intrathecal, and intraventricular injections. Enteral administration modalities include, for example, oral (including buccal and sublingual) and rectal administration. Transepithelial administration modalities include, for example, transmucosal administration and transdermal administration. Transmucosal administration includes, for example, enteral administration as well as nasal, inhalation, and deep lung administration; vaginal administration; and rectal administration. Transdermal administration includes passive or active transdermal or transcutaneous modalities, including, for example, patches and iontophoresis devices, as well as topical application of pastes, salves, or ointments. Surgical techniques include implantation of depot (reservoir) compositions, osmotic pumps, and the like.

The pharmaceutical compositions are formulated to contain suitable pharmaceutically acceptable carriers, and may optionally comprise excipients and auxiliaries that facilitate processing of the active compounds into preparations that can be used pharmaceutically. The administration modality will generally determine the nature of the carrier. For example, formulations for parenteral administration may comprise aqueous solutions of the active compounds in water-soluble form. Carriers suitable for parenteral administration can be selected from among saline, buffered saline, dextrose, water, and other physiologically compatible solutions. Preferred carriers for parenteral administration are physiologically compatible buffers such as Hank's solution, Ringer's solutions, or physiologically buffered saline. For tissue or cellular administration, penetrants appropriate to the particular barrier to be permeated are used in the formulation. Such penetrants are generally known in the art. For preparations comprising proteins, the formulation may include stabilizing materials, such as polyols (e.g., sucrose) and/or surfactants (e.g., nonionic surfactants), and the like.

Alternatively, formulations for parenteral use may comprise suspensions of the active compounds prepared as appropriate oily injection suspensions. Suitable lipophilic solvents or vehicles include fatty oils, such as sesame oil, and synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Emulsions, e.g., oil-in-water and water-in-oil dispersions, can also be used, optionally stabilized by an emulsifying agent or dispersant (surface-active materials; surfactants). Liposomes containing the active agent may also be employed for parenteral administration.

Alternatively, the pharmaceutical compositions comprising the agent in dosages suitable for oral administration can be formulated using pharmaceutically acceptable carriers well known in the art. The preparations formulated for oral administration may be in the form of tablets, pills, capsules, cachets, dragees, lozenges, liquids, gels, syrups, slurries, suspensions, or powders. To illustrate, pharmaceutical preparations for oral use can be obtained by combining the active compounds with a solid excipient, optionally grinding the resulting mixture, and processing the mixture of granules, after adding suitable auxiliaries if desired, to obtain tablets or dragee cores. Note that oral formulations may employ liquid carriers similar in type to those described for parenteral use, e.g., buffered aqueous solutions, suspensions, and the like.

Preferred oral formulations include tablets, dragees, and gelatin capsules. These preparations may contain one or excipients, which include, without limitation:

a) diluents such as sugars, including lactose, dextrose, sucrose, mannitol, or sorbitol;

b) binders such as magnesium aluminum silicate, starch from corn, wheat, rice, potato, etc.;

c) cellulose materials such as methyl cellulose, hydroxypropylmethyl cellulose, and sodium carboxymethyl cellulose, polyvinyl pyrrolidone, gums such as gum arabic and gum tragacanth, and proteins such as gelatin and collagen;

d) disintegrating or solubilizing agents such as cross-linked polyvinyl pyrrolidone, starches, agar, alginic acid or a salt thereof such as sodium alginate, or effervescent compositions;

e) lubricants such as silica, talc, stearic acid or its magnesium or calcium salt, and polyethylene glycol;

f) flavorants, and sweeteners;

g) colorants or pigments, e.g., to identify the product or to characterize the quantity (dosage) of active compound; and h) other ingredients such as preservatives, stabilizers, swelling agents, emulsifying agents, solution promoters, salts for regulating osmotic pressure, and buffers.

Gelatin capsules include push-fit capsules made of gelatin, as well as soft, sealed capsules made of gelatin and a coating such as glycerol or sorbitol. Push-fit capsules can contain the active ingredient(s) mixed with fillers, binders, lubricants, and/or stabilizers, etc. In soft capsules, the active compounds may be dissolved or suspended in suitable fluids, such as fatty oils, liquid paraffin, or liquid polyethylene glycol with or without stabilizers.

Dragée cores can be provided with suitable coatings such as concentrated sugar solutions, which may also contain gum arabic, talc, polyvinyl pyrrolidone, carbopol gel, polyethylene glycol, and/or titanium dioxide, lacquer solutions, and suitable organic solvents or solvent mixtures.

The pharmaceutical composition may be provided as a salt of the active agent, which can be formed with many acids, including but not limited to hydrochloric, sulfuric, acetic, lactic, tartaric, malic, succinic, etc. Salts tend to be more soluble in aqueous or other protonic solvents that are the corresponding free base forms.

As noted above, the characteristics of the agent itself and the formulation of the agent can influence the physical state, stability, rate of in vivo release, and rate of in vivo clearance of the administered agent. Such pharmacokinetic and pharmacodynamic information can be collected through pre-clinical in vitro and in vivo studies, later confirmed in humans during the course of clinical trials. Thus, for any compound used in the method of the invention, a therapeutically effective dose in mammals, particularly humans, can be estimated initially from biochemical and/or cell-based assays. Then, dosage can be formulated in animal models to achieve a desirable circulating concentration range (e.g., of the modulator). As human studies are conducted, further information will emerge regarding the appropriate dosage levels and duration of treatment for various diseases and conditions.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the "therapeutic index," which is typically expressed as the ratio $LD_{50}/ED_{50}$. Compounds that exhibit large therapeutic indices are preferred. The data obtained from such cell culture assays and additional animal studies can be used in formulating a range of dosage for human use. The dosage of such compounds lies preferably within a range of circulating concentrations that include the $ED_{50}$ with little or no toxicity.

For the method of the invention, any effective administration regimen regulating the timing and sequence of doses may be used. Doses of the agent preferably include pharmaceutical dosage units comprising an effective amount of the agent. As used herein, "effective amount" refers to an amount sufficient to provide or modulate interaction of amyloid β or its aggregates with the sodium channel through administration of one or more of the pharmaceutical dosage units.

Exemplary dosage levels for a human subject are of the order of from about 0.001 milligram of active agent per kilogram body weight (mg/kg) to about 100 mg/kg. Typically, dosage units of the active agent comprise from about 0.01 mg to about 10,000 mg, preferably from about 0.1 mg to about 1,000 mg, depending upon the indication, route of administration, etc. Depending on the route of administration, a suitable dose may be calculated according to body weight, body surface area, or organ size. The final dosage regimen will be determined by the attending physician in view of good medical practice, considering various factors that modify the action of drugs, e.g., the agent's specific activity, the severity of the disease state, the responsiveness of the patient, the age, condition, body weight, sex, and diet of the patient, the severity of any infection, and the like. Additional factors that may be taken into account include time and frequency of administration, drug combination(s), reaction sensitivities, and tolerance/response to therapy. Further refinement of the dosage appropriate for treatment involving any of the formulations mentioned herein is done routinely by the skilled practitioner without undue experimentation, especially in light of the dosage information and assays disclosed, as well as the pharmacokinetic data observed in yeast clinical trials. Appropriate dosages may be ascertained through use of established assays for determining concentration of the agent in a body fluid or other sample together with dose response data.

The frequency of dosing will depend on the pharmacokinetic parameters of the agent and the route of administration. Dosage and administration are adjusted to provide sufficient levels of the active moiety or to maintain the desired effect. Accordingly, the pharmaceutical compositions can be administered in a single dose, multiple discrete doses, continuous infusion, sustained release depots, or combinations thereof, as required to maintain desired minimum level of the agent. Short-acting pharmaceutical compositions (i.e., short half-life) can be administered once a day or more than once a day (e.g., two, three, or four times a day). Long acting pharmaceutical compositions might be administered every 3 to 4 days, every week, or once every two weeks. Pumps, such as subcutaneous, intraperitoneal, or subdural pumps, may be preferred for continuous infusion.

Compositions comprising an active agent of the invention formulated in a pharmaceutical acceptable carrier may be prepared, placed in an appropriate container, and labeled for treatment of an indicated condition. Conditions indicated on the label may include, but are not limited to, treatment and diagnosis of Alzheimer's disease and prion disease. Kits are also contemplated, wherein the kit comprises a dosage form of a pharmaceutical composition and a package insert containing instructions for use of the composition in treatment of a medical condition.

EXAMPLES

The following examples further illustrate the present invention but should not be construed as in any way limiting its scope.

The examples presuppose an understanding of conventional methods well-known to those persons having ordinary skill in the art to which the examples pertain, e.g., the techniques for isolation and electrophysiological assessment of cells (e.g., neuronal cells). Such methods are described in detail in numerous publications including, for example, in Hille, In, *Ionic Channels of Excitable Membranes.* Sinauer Associates, Inc. (1992). The contents of this publication and other publications cited in the Examples are incorporated by reference, in their entirety.

For all studies as described herein, single neurons freshly dissociated from adult rats (Chad et al, In, *Cellular Neurobiology,* Ed. J. Chad and H. Wheal, Oxford University Press (1991)) were examined using the suction pipette method (Lee et al., *J. Neurosc. Methods,* 2; 51–78 (1980)) under current- or voltage-clamp, with use of an Axopatch 200 Amplifier (Axon Instruments, Foster City, Calif.). Amyloid β1–40 was obtained from Polypeptide Laboratories, Torrance, Calif., or from Bachem Biochemica, Heidelberg, Germany.

Shaken aggregation assays (i.e., as in Examples 1–4) were performed as described previously (e.g., Findeis et al., *Biochemistry,* 38, 6791–6800 (1999)). This aggregation performed prior to use of the aggregated amyloid for contacting cells was done in the same media as the cells were contained, i.e., Hank's Balanced Salt Solution. Aggregation of amyloid for kinetic studies (i.e., as in Example 5), was done in a buffer composed of 10 mM phosphate, 100 mM NaCl, pH 7.4. In each case, aggregation was carried out in 96 well plates containing 25–50 µM amyloid β 1–40 in a final volume of 250 µl. The plates were rotary shaken using a titer plate shaker (Lab-Line Model 4623, Lab-Line Inst., Melrose Park, Ill.) at a rate of from about 700 to 800 rpm (monitored by a tachometer) to induce aggregation. At given times, the turbidities of the reaction mixture were read by measuring light scattering at 405 nm in a Molecular Devices (Menlo Park, Calif.) Vmax Microplate Reader. For all the Examples, the aggregating material was removed at timed intervals and added to isolated neurons to examine its effect.

Prior to aggregation, to prepare amyloid β in monomeric form, amyloid β 1–40 (e.g., to be used as an HPLC standard) was treated with hexafluoroisopropyl alcohol (HFIPA), which had been dried over Molecular Sieve, Type 4A, at 4° C. and centrifuged at 15,000×g for 10 minutes to remove molecular sieve dust. For aggregation assays, the peptide was dissolved in the HFIPA at 8 mg/ml and held in the solvent for 18 to 24 hours to disaggregate any preformed particles. Following this monomerization step, 20 µl aliquots of this solution were flash frozen in liquid nitrogen and stored at −195° C. until use. Without thawing, the HFIPA in the peptide was removed by lyophilization under dry ice. Complete removal of the HFIPA without thawing was essential to achieve non-aggregated starting material, e.g., if the frozen pellets melt prior complete lyophilization, there is a high probability that multimers will reform. The lyophilized Aβ 1–40 was dissolved in anhydrous DMSO (usually 20 μl) and sonicated in a bath sonicator for 15 minutes. Since the above procedure is lengthy and cumbersome, for some experiments, the acid treatment procedure wherein the Aβ 1–40 is dissolved in 0.1% acetic acid prior to aggregation (Findeis et. al., supra) was employed, and was found to be acceptable for peptide randomization.

Example 1

In this experiment, the firing patterns of isolated adult rat cortical and hippocampal neurons were examined using an Axopatch 200 Amplifier in the presence or absence of amyloid β 1–40 peptide.

In current-clamp, the resting membrane potential and action potentials of single neurons were continuously monitored for at least 10–20 minutes until the neuronal activity became stable. Then, 10–50 μM amyloid β 1–40 preaggregated for different times was added to the neuron slowly without causing any flow artifact. In 5–10 minutes, resting potentials started to move to either a depolarized or hyperpolarized direction, depending on the neuronal type examined. However, the common effect was the slow disappearance of spontaneous or evoked action potentials. After about 20–30 minutes of peptide exposure, the action potentials in most of the neurons examined disappeared altogether. These amyloid β treated neurons became silent, non-functional, and in a vegetative state after prolonged exposure (i.e., about 30 to 60 minutes) to amyloid β.

Figures 2A, 2B, 2C:
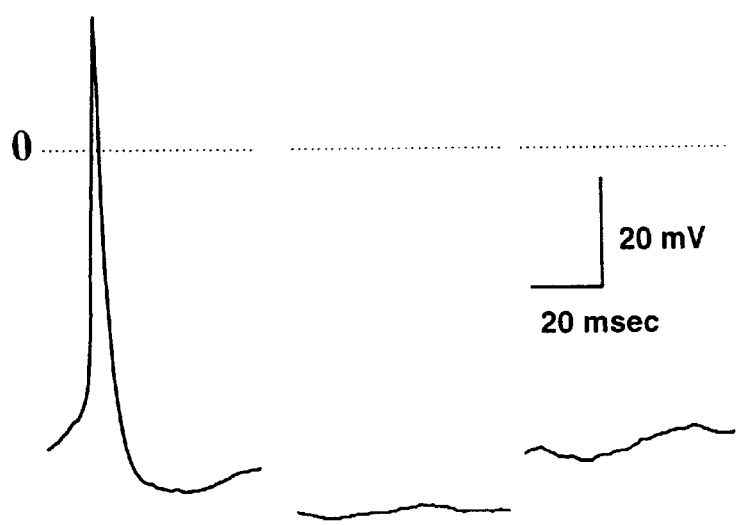
FIGS. 2A–C are recordings taken from an Axopatch 200 Amplifier which show changes of an action potential recorded from a single hippocampal neuron: (A) in the absence of amyloid β 1–40 peptide; (B) in the presence of 11.5 μM amyloid β 1–40 peptide; or (C) following washing of the neuron with peptide-free solution.

These results are depicted in FIGS. 1A–C for cortical neurons, and FIGS. 2A–C for hippocampal neurons. These results confirm an abrogation of action potentials in cortical and hippocampal neurons with addition to the neuron of 11.5 μM amyloid β 1–40.

These results thus confirm that amyloid β 1–40 peptide alters the firing patterns of adult rat cortical and hippocampal neurons.

Example 2

In this experiment, the effect of amyloid β 1–40 on the fast inward sodium current ($I_{Na}$) of isolated rat hippocampal neurons was studied using an Axopatch 200 Amplifier.

Figures 3A, 3B, 3C:
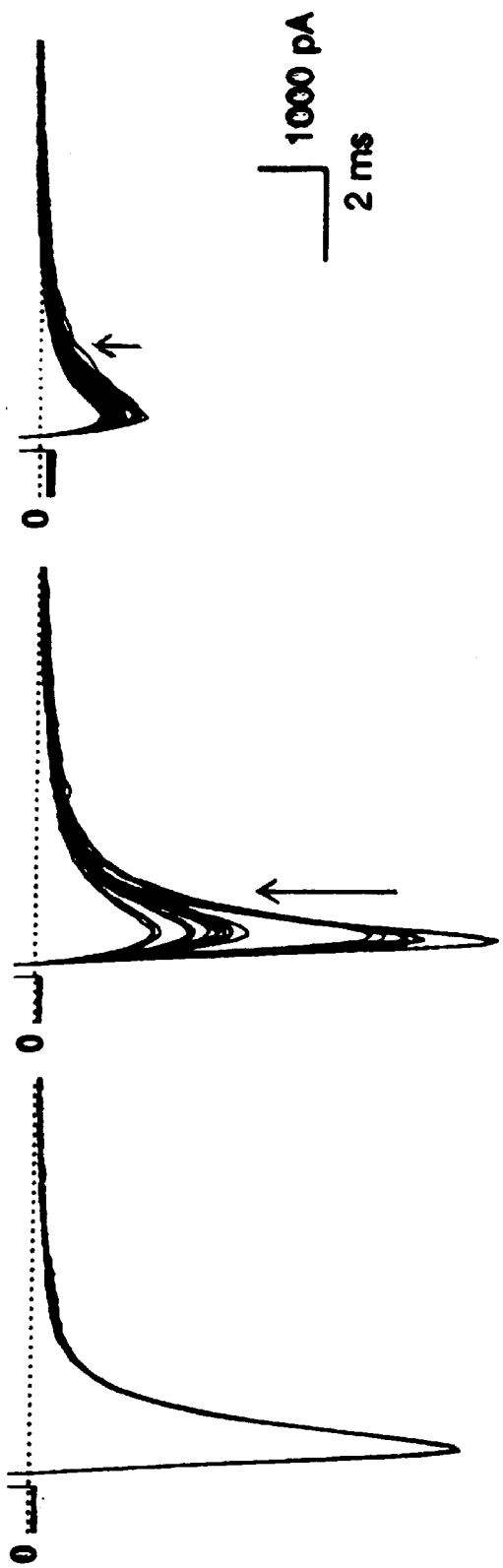
FIGS. 3A–C are recordings taken from an Axopatch 200 Amplifier which show the progressive reduction in a fast inward sodium current of a hippocampal neuron elicited by step potential change from −80 mV (millivolt) to −30 mV in the absence of amyloid β 1–40 (FIG. 3A), in the presence of 50 μM amyloid β1–40 following about 90 minutes shake-induced amyloid 13 aggregation (FIG. 3B), and in the presence of 50 μM amyloid β 1–40 following about 120 minutes shake-induced amyloid β aggregation (FIG. 3C). The effect of the peptide cannot wash out. The arrow indicates the direction of progressive current depression by the peptide.
Figure 4:
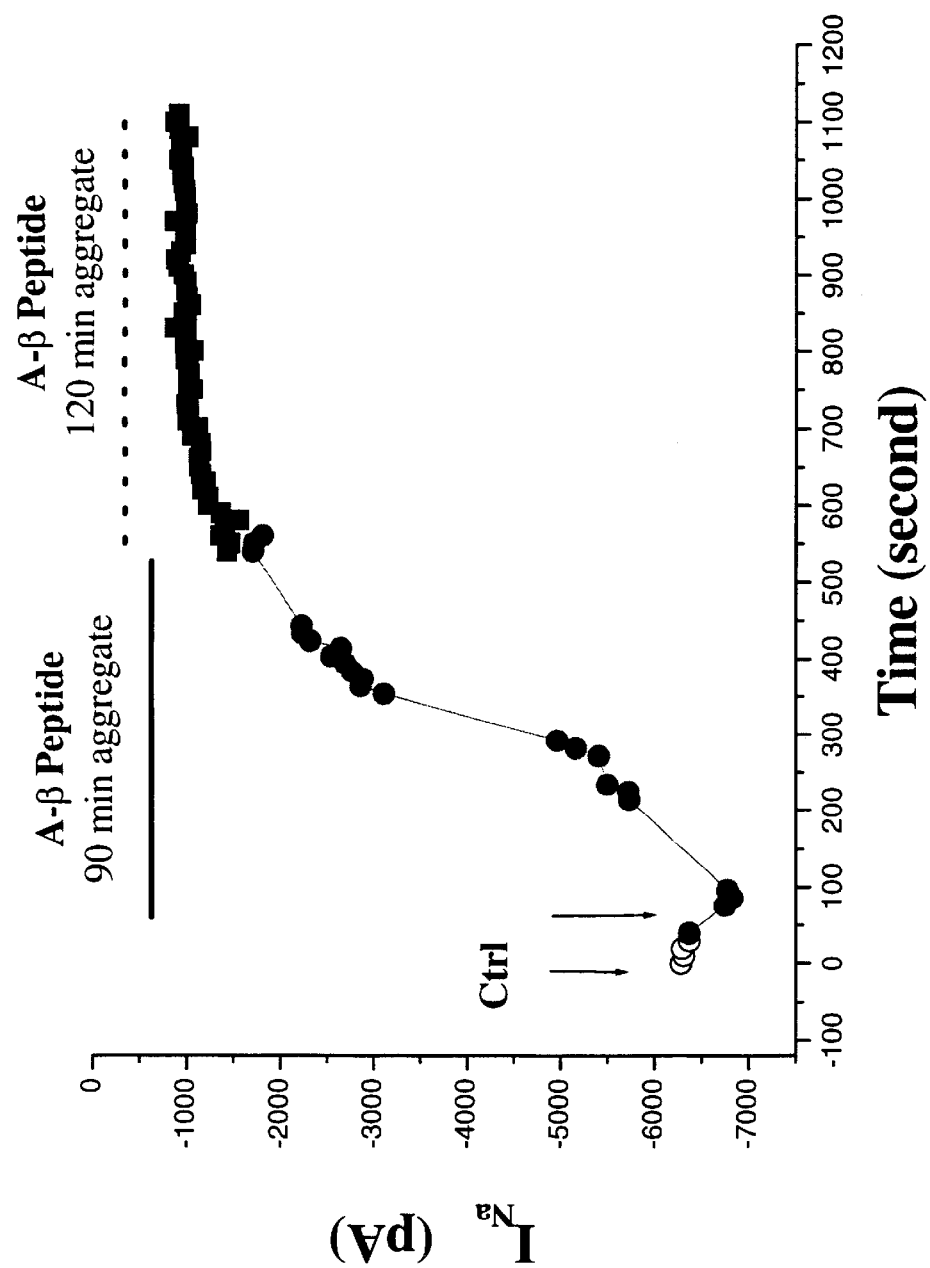
FIG. 4 is a graph which shows the progressive change of peak amplitude of inward sodium current ($I_{na}$) measured in pico ampere (pA) (Y-axis) with time (second) (X-axis), in the absence of amyloid β 1–40 (open circles), in the presence of 50 μM amyloid β 1–40 following about 90 minutes of shake-induced amyloid β aggregation (solid circles), and in the presence of 50 μM amyloid β 1–40 following about 120 minutes shake-induced amyloid β aggregation (solid squares). The readings were from the same experiment as in FIG. 3A–C.

These studies were done by voltage-clamping the neurons at a holding potential of −50 to −80 mV where the sodium channels were fully activated. Again, a stable control was obtained. Then, 10–50 μM amyloid β 1–40 aggregated for various times at room temperature (23° C.) in 10 mM phosphate, 100 mM NaCl at pH 7.4 was applied to the neurons. In about 5–30 minutes, approximately the same time frame for the action potentials to disappear, the fast inward sodium current was blocked by amyloid β 1–40 by as much as 90%, as can be seen by comparing results in FIG. 3A (control) with those in FIG. 3B (90 minute aggregated amyloid β) and FIG. 3C (120 minute aggregated amyloid β). The progressive change of peak amplitude of inward sodium current for the same experiments with hippocampal neurons is graphed in FIG. 4 for 90 minute aggregated amyloid β (solid circles), and 120 minute aggregated amyloid β (solid squares).

Also, at this time, switching back to current-clamp, the neuron failed to fire action potentials (as can be seen in FIG. 1B and FIG. 2B), thus confirming that the mechanism of action potential elimination by amyloid β 1–40 is through blockade of the fast inward sodium channels.

Figures 5A, 5B, 5C, 5D:
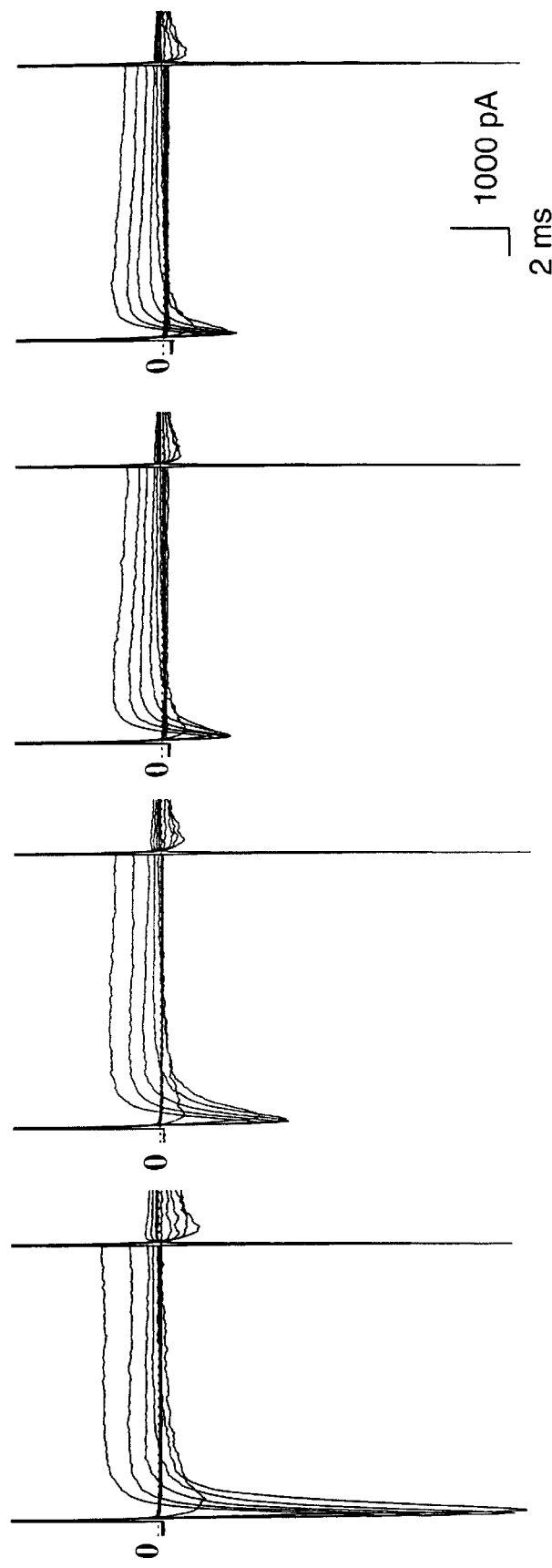
FIGS. 5A–D are recordings taken from an Axopatch 200 Amplifier which show the effect of amyloid β 1–40 on the fast inward sodium current of a hippocampal neuron over a broad range of membrane potentials ranging from about −50 to +20 m, with each panel showing eight fast inward sodium current traces superimposed on the same time frame elicited by step potential changes from a holding potential of −80 mV to −50 mV, then in 10 mV increments, to +20 mV in the absence of amyloid β1–40 (FIG. 5A), in the presence of 50 μM amyloid β 1–40 following about 90 minutes shake-induced amyloid β aggregation (FIG. 5B), in the presence of 50 μM amyloid β 1–40 following about 120 minutes shake-induced amyloid β aggregation (FIG. 5C), and following wash out of the peptide (FIG. 5D). The effect of amyloid β 1–40 cannot wash out.
Figure 6:
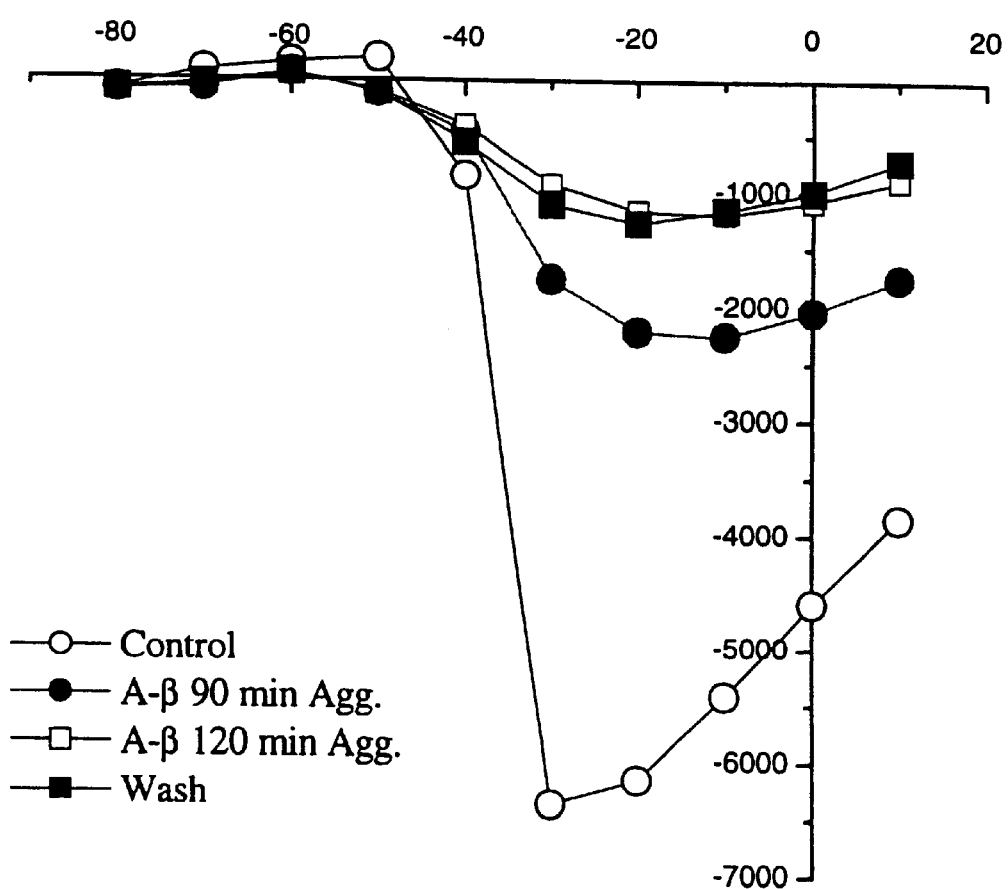
FIG. 6 is a graph which shows peak amplitude of fast inward sodium current in pA (Y-axis) over a broad range of membrane potential in mV (X-axis) in the absence of amyloid β 1–40 (open circles), in the presence of 50 μM amyloid β 1–40 following about 90 minutes shake-induced amyloid β aggregation (solid circles), in the presence of 50 μM amyloid β 1–40 following about 120 minutes shake-induced amyloid β aggregation (open squares), and following wash out of the peptide (solid squares). The readings were from the same experiment as in FIGS. 5A–D.

This further can be seen for rat hippocampal neurons, by comparing readings obtained for resting potential in FIG. 5A (control) and FIG. 5D (wash condition) with those obtained in FIG. 5B (90 minute aggregated amyloid β) and FIG. 5C (120 minute aggregated amyloid β). For the same experiment, switching back to current-clamp, the neuron failed to fire action potentials, as can be seen in FIG. 6 for 90 minute aggregated amyloid β (solid circles), and 120 minute aggregated amyloid β (open squares).

Figures 7A, 7B, 7C:
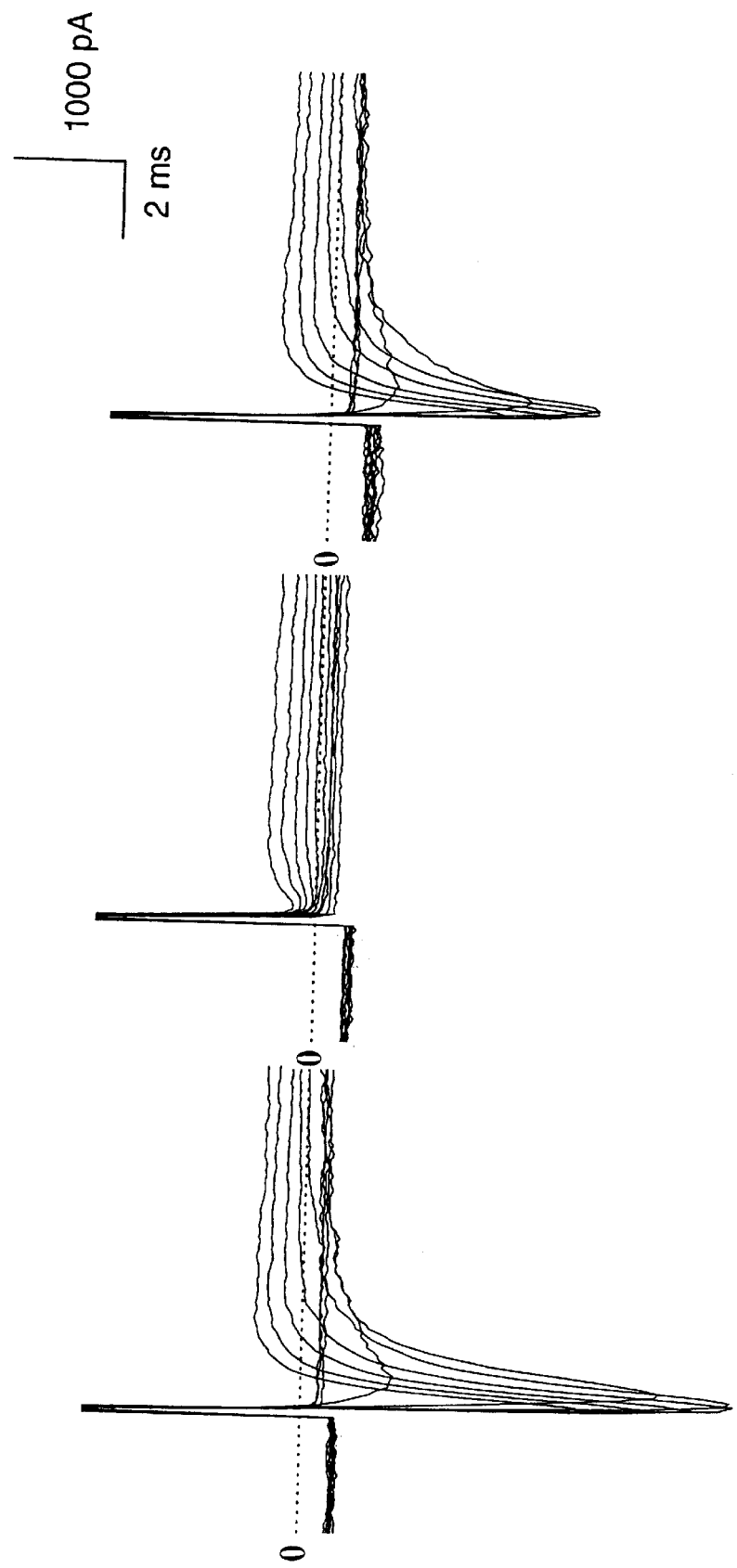
FIGS. 7A–C are recordings taken from an Axopatch 200 Amplifier which show superimposed sodium current traces of a hippocampal neuron elicited from a holding potential of −80 mV to −70 mV, and then at 10 mV increments to +10 mV, and obtained in the absence of the specific fast inward sodium channel blocker tetrodotoxin (TTX) (FIG. 7A), in the presence of 1 μM TTX (FIG. 7B), and in washing out of TTX (FIG. 7C).
Figure 8:
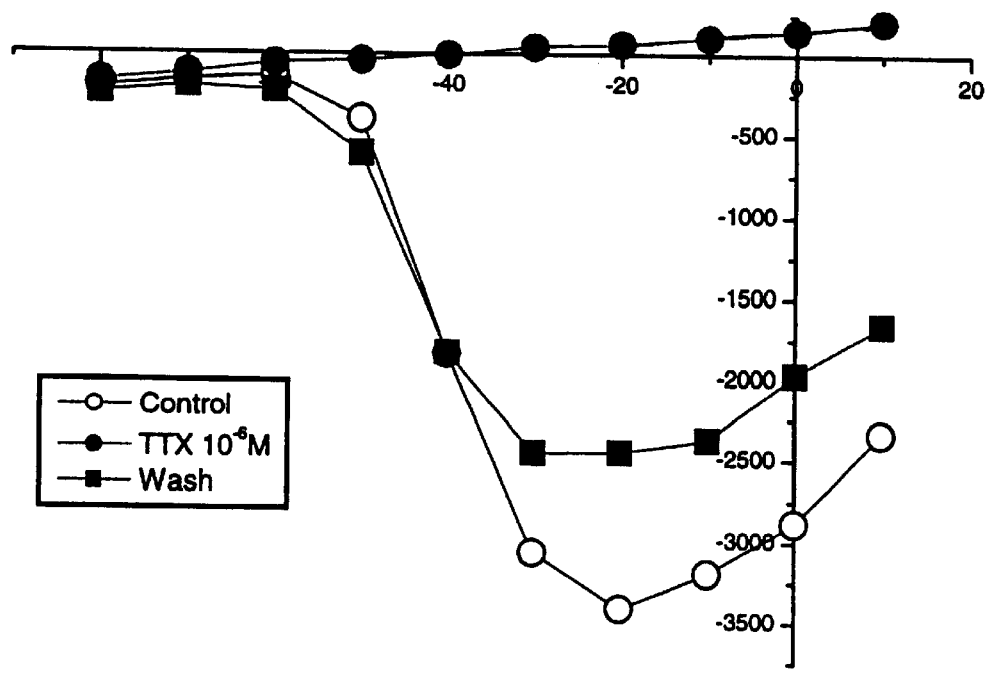
FIG. 8 is a graph which shows peak amplitude of fast inward sodium current in pA (Y-axis) over a broad range of membrane potential in mV (X-axis) in the absence of TTX (open circles), in the presence of 1 μM TTX (solid circles), and following wash out of TTX (solid squares). The readings were from the same experiment as in FIGS. 7A–C.

Additionally, it was shown that this fast inward sodium current is sensitive to tetrodotoxin (TTX). This can be seen by comparing sodium current traces obtained from hippocampal neurons in FIGS. 7A (control, having no TTX exposure) and FIG. 7C (wash) with those obtained in FIG. 7B ($10^{-6}$ M TTX). For the same experiment, changes of peak amplitude of inward sodium current over a broad potential range from −80 mV to +10 mV are shown in FIG. 8 for the control (open circles) and wash condition (closed squares) as compared to the neurons exposed to TTX (closed circles).

These results confirm that amyloid β 1–40 inhibits the fast inward sodium current ($I_{Na}$). This is a novel and unexpected finding, since prior results focused on the impact of amyloid β on calcium and/or potassium channels. Furthermore, the results confirm that the amyloid β 1–40-targeted a fast inward sodium channel and is sensitive to tetrodotoxin. However, other types of sodium channels may also be involved, and/or may be sensitive to the negative effects of amyloid β.

Example 3

In this experiment, the effect of amyloid β 1–40 on the calcium ion channel was studied using the methods described in Experiment 2 for the sodium channel.

Figures 9A, 9B:
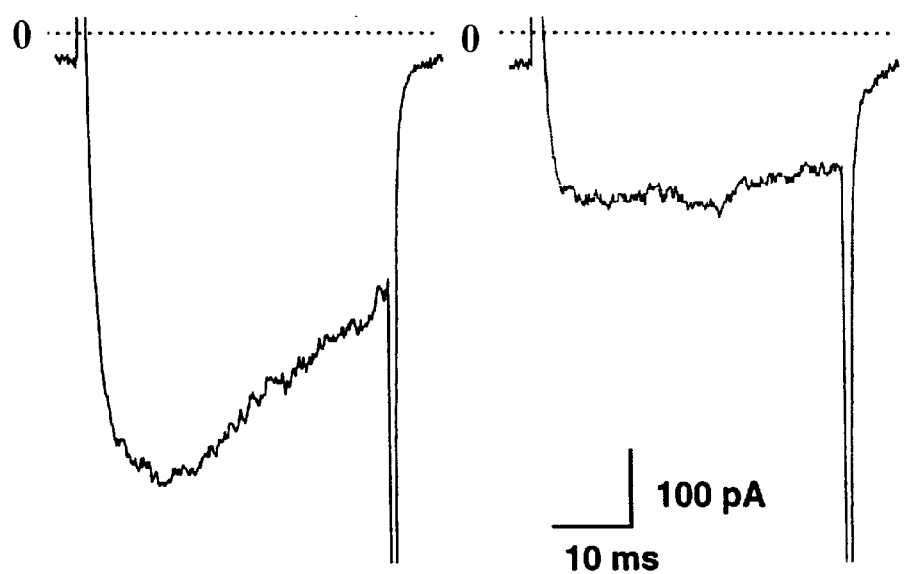
FIGS. 9A–B are recordings taken from an Axopatch 200 Amplifier which show a single calcium current elicited in isolated hippocampal neurons from a holding potential of −40 mV to +10 mV, in the absence of amyloid β 1–40 (FIG. 9A), and in the presence of 50 μM amyloid β 1–40 peptide following about 70 minutes shake-induced amyloid β aggregation (FIG. 9B).
Figure 10:
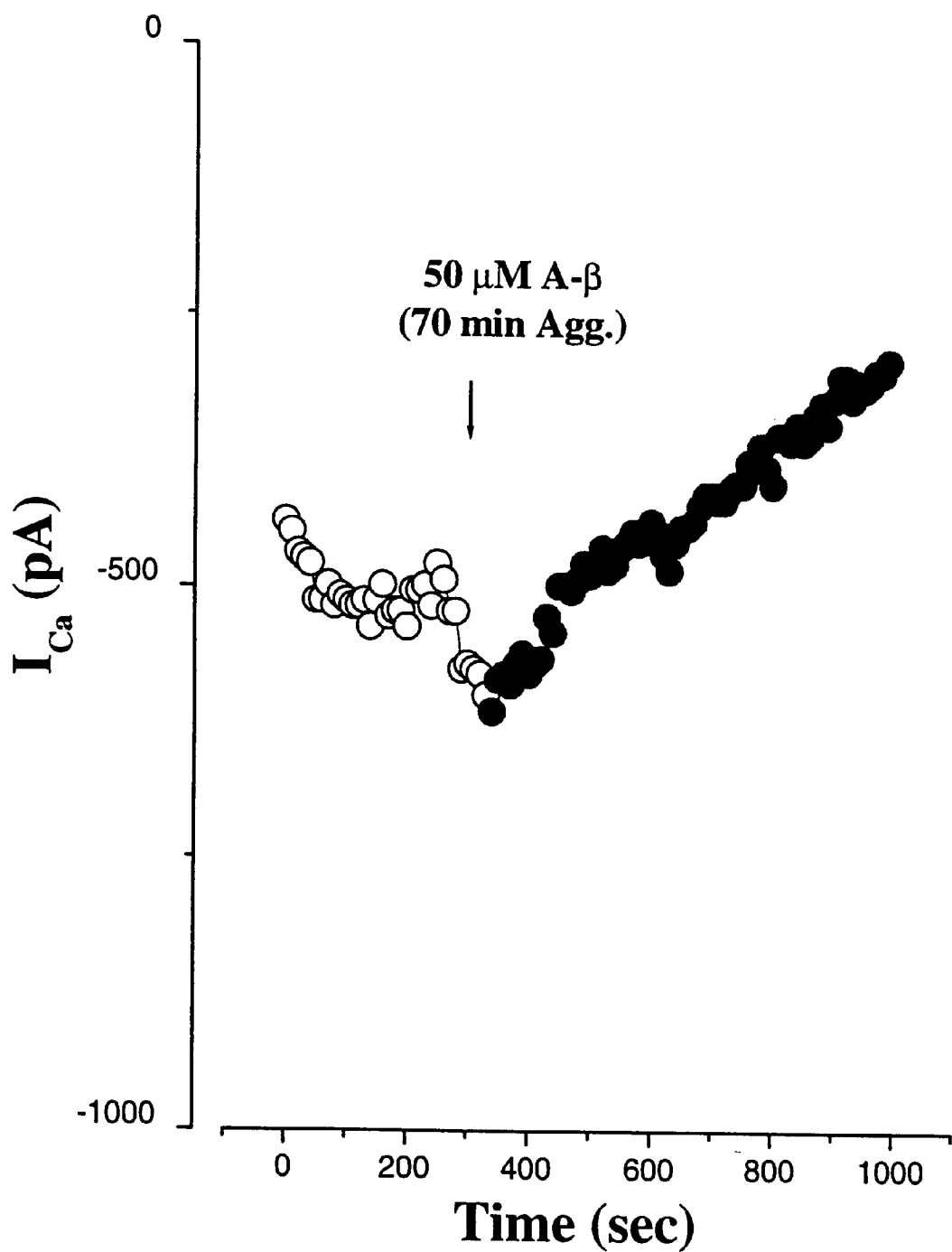
FIG. 10 is a graph which shows peak calcium current ($I_{ca}$) amplitude in pA (Y-axis) over time in seconds (sec) (X-axis) in the absence of amyloid β (open circles), and in the presence of 50 μM amyloid β 1–40 following about 70 minutes shake-induced amyloid β aggregation (solid circles). The readings were from the same experiment as in FIGS. 9A–B.

The amyloid β 1–40 peptide also was found to depress neuronal inward calcium currents (see, FIGS. 9A–B and FIG. 10). However, the calcium channel may be more resistant to the inhibitory action of amyloid β 1–40.

These results confirm that amyloid β 1–40 affects neuronal calcium currents.

Example 4

In this experiment, the effect of amyloid β 1–40 on the potassium ion channel was studied using the methods described in Experiment 2 for the sodium channel.

Figure 11:
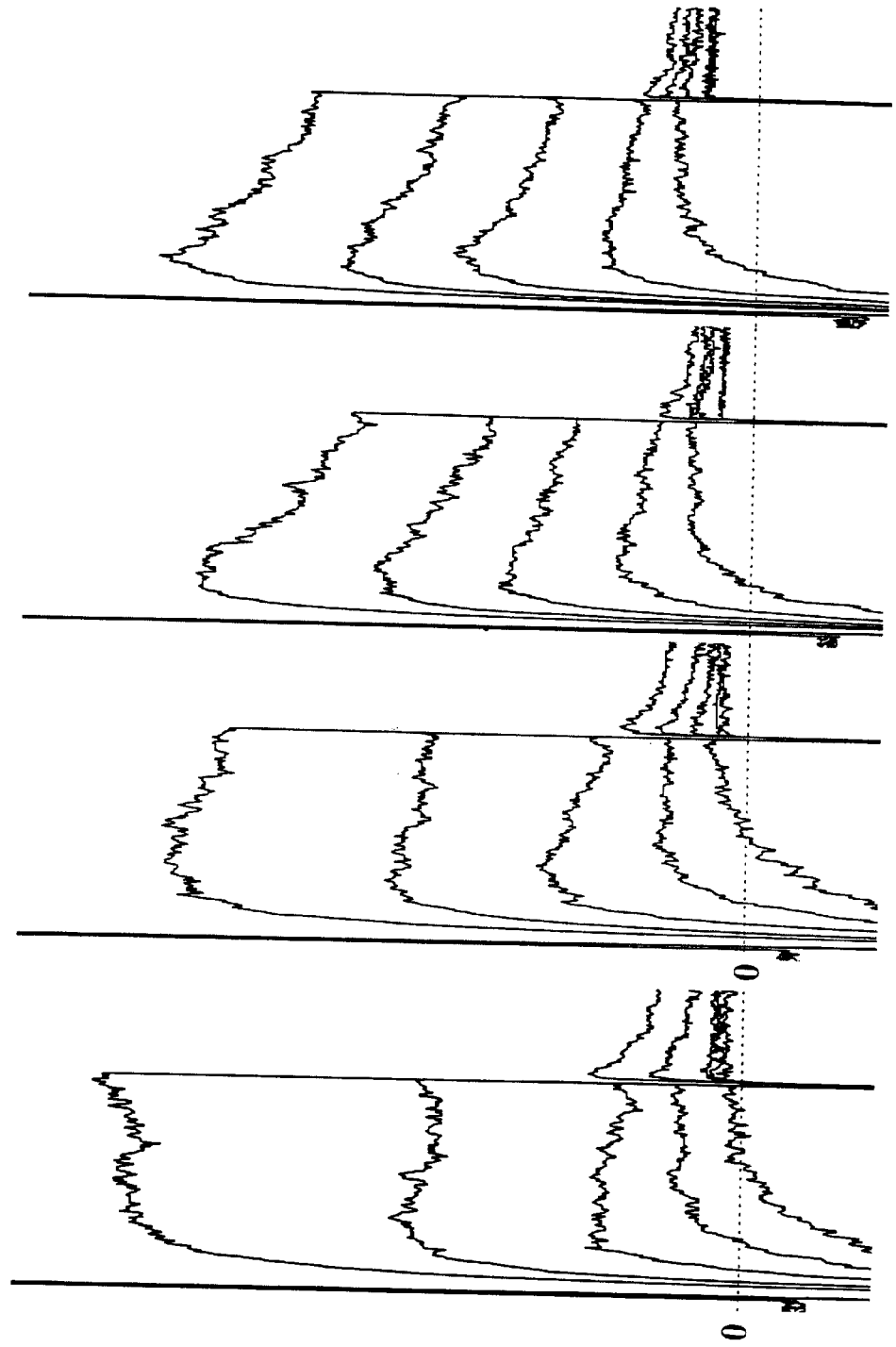
FIGS. 11A–D are recordings taken from an Axopatch 200 Amplifier which show potassium currents elicited by a step potential from a holding potential of −40 mV to +10 mV, in 10 mV increments in the absence of amyloid β 1–40 (FIG. 11A), in the presence of 50 μM amyloid β 1–40 following about 90 minutes shake-induced amyloid β aggregation (FIG. 11B), in the presence of 50 μM amyloid β 1–40 following about 120 minutes shake-induced amyloid β aggregation (FIG. 11C), and following wash out of the peptide (FIG. 11D).
Figure 12:
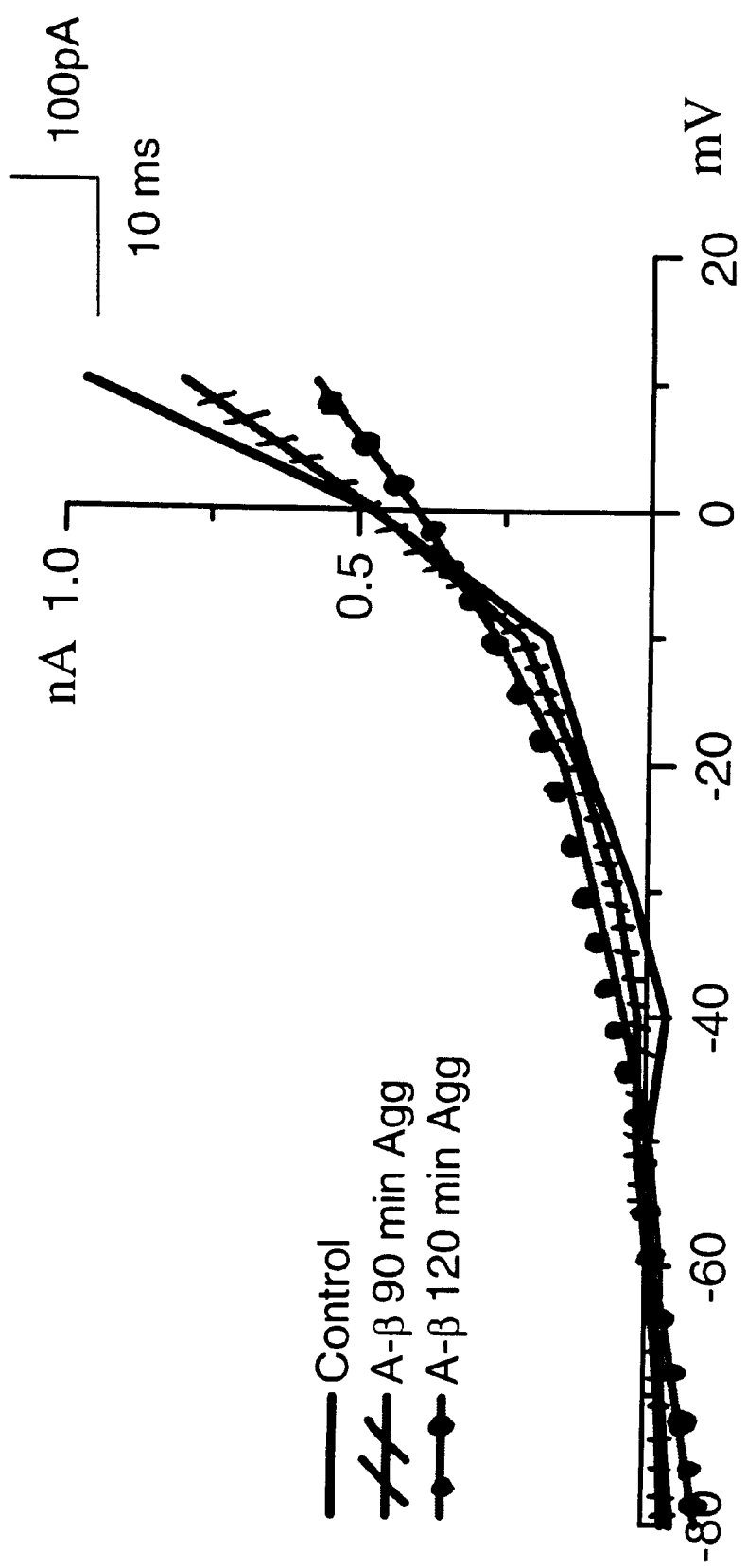
FIG. 12 is a graph which shows peak amplitude of potassium currents in nanoampere (nA) (Y-axis) over a broad range of membrane potential in mV (X-axis) in the absence of amyloid β 1–40 (solid line), in the presence of 50 μM amyloid β 1–40 following about 90 minutes shake-induced amyloid β aggregation (cross-hatched line), and in the presence of 50 μM amyloid β 1–40 following about 120 minutes shake-induced amyloid β aggregation (dotted line). The readings were from the same experiments as in FIG. 11A–D.

In voltage-clamp, within the first 2–5 minutes, in some cells the peptide induced an outward holding current measuring about 10–50 pA, but this small current was enough to hyperpolarize the resting membrane potential from −50 mV to −90 mV. In other cells, the peptide instead caused a gradual depolarization to about −40 mV due to a slight inhibition of the outward holding current. In all cells, amyloid β 1–40 blocked the delayed outward potassium current by about 30–40% at all step potentials. The corresponding action potential measurement showed that this effect resulted in broadening of normal action potential duration (shown in FIG. 1B). These results are presented in FIGS. 11A–B and FIG. 12.

These results thus confirm that amyloid β 1–40 affects major neuronal potassium currents.

Example 5

In this experiment, the relationship between amyloid β 1–40 aggregation and its ability to impact a variety of parameters as described herein, including sodium channel activity, was studied.

By way of background, the kinetics of amyloid β peptide's spontaneous aggregation are characterized by a long lag phase in which at least a small quantity of the aggregate can be detected by thioflavine T fluorescence. The lag phase is followed by a log phase which is rapid and results in the deposition of peptide until the solution is totally depleted of amyloid β monomers. The rapid acceleration (propagation) of fibril growth occurs from a preformed nucleus. The most important step in the whole process is nucleation from which fibril formation proceeds rapidly. Inhibition of nucleation halts the entire process and an assay capable of measuring this early event would be highly desirable. The sharp, exponential rise during the propagation phase is indicative of the presence of higher order aggregation and growth of the aggregate. The kinetics of spontaneous aggregation were studied from experiments done herein, as well as making use of literature reported data (e.g., Lansbury et al., *Arzn. For. Drug Research*, 45, 432–434 (1995); Pillot et al., *Eur. J Biochem.*, 243, 650–659 (1997)).

For these studies, in order to learn more about the form of the amyloid β peptide having the greatest ability to deleteriously impact various cell parameters, kinetic experiments were first performed to establish the time course of the formation of the β-turn form of Aβ 1–40 (activated monomer), and of the tetramer. Then, aliquots of the peptide were taken at select time points from the actively aggregating solution of Aβ 1–40, and were added to isolated rat hippocampal neurons. The impact of various aggregated forms of Aβ were studied using a variety of tests including: (1) resting membrane potentials; (2) action potentials; (3) fast inward sodium channels (TTX-sensitive); (4) calcium channels; and (5) outward potassium channels.

The data obtained from the kinetic studies was assessed using several multiple order kinetic models for spontaneous aggregation. It was found that the simplest scheme (as set out in Equations 1–3 below) consistent with these data is one in which the nonnucleating, random coil structure, monomeric peptide (inactive A) is converted to an active, nucleatable form (B) according to the equation:

$$A \xrightarrow{k_l} B \quad \text{(Equation 1)}$$

B then oligomerizes to a tetrameric intermediate (C):

$$4B \xrightarrow{k_n} C \quad \text{(Equation 2)}$$

that binds species A rapidly to form the insoluble fibrillar structure (P):

$$C + A \xrightarrow[k_p]{\text{Fast}} C + P \quad \text{(Equation 3)}$$

The system of differential equations describing this model is:

$$\frac{dA}{dt} = -k_l A - k_p C^* A \quad \text{(Equation 4)}$$

$$\frac{dB}{dt} = k_l A - k_n B^4 \quad \text{(Equation 5)}$$

$$\frac{dC}{dt} = k_n B^4 - k_p C^* A \quad \text{(Equation 6)}$$

$$\frac{dP}{dt} = k_p C^* A \quad \text{(Equation 7)}$$

Because the solution to the differential equations 4–7 is nonintegrable, the data had to be fit using a proper nonlinear least squares fitting algorithm chained to a fifth-order Runge-Kutta numerical integration algorithm. The nonlinear least squares fitting program used in this case was one written by Dr. Ferenc Kézdy (Pharmacia & Upjohn, Kalmazoo, Mich.).

The data are consistent with a model of a slow change of the peptide in solution from an inactive, non-nucleating form to an active form that can initiate amyloid β aggregation. The analysis showed that a tetramer form of the peptide is responsible for nucleation. After nucleation, the determining factor in the steep portion of the kinetics is propagation, and the compound that forms the tetramer reaches a steady state at this point. The kinetics of all spontaneous aggregation experiments performed herein, and by others (Lansbury et al., *Arzn. For. Drug Res.*, 45, 432–434 (1991); Pillot et al., *Eur. J Biochem.*, 243, 650–659 (1997)) were consistent only with this model. The results may suggest that the deleterious impact (e.g., cell killing) of the amyloid peptide is due to the amyloid tetramer forming a pore in biological membranes, similar to the toxic, tetrameric form of melittin.

Following the kinetic studies, aliquots of amyloid β were taken at select time points from the actively aggregating solution of Aβ 1–40, and were added to rat hippocampal cortical neurons. The inward sodium current was then measured continuously. The percentage decrease in the inward sodium current was determined for each test point as the rate at which the sodium current was generated. Additionally, the various aggregated forms of Aβ were assessed for any impact on resting membrane potential, action potential, calcium channel, and outward potassium channel.

Figure 13:
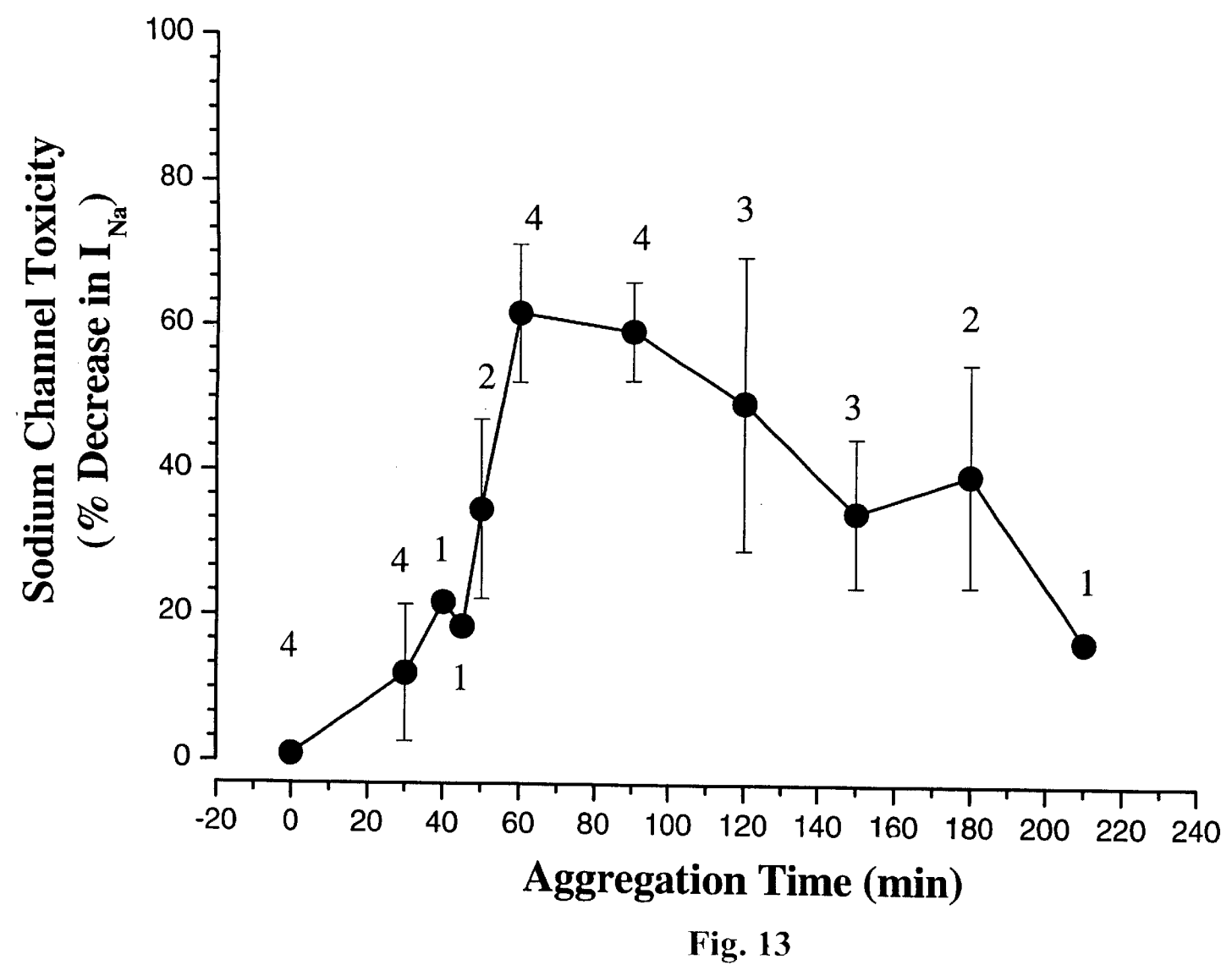

Monomers of amyloid β 1–40 did not show significant impact on the parameters assessed. But as the monomers aggregate, to form dimers, tetramers and then polymers, the ability of amyloid β 1–40 to negatively impact channel activity then appeared, and increased exponentially, approximately following the time course of peptide aggregation. The fraction having the greatest negative impact on channel activity appeared just before the monomers' complete disappearance and saturation of peptide aggregation. After reaching the saturation, the peak impact decreased, but was still above the 50% inhibition level of the fast inward sodium channels (shown in FIG. 13; which is the mean values of four experiments with 29 cells each).

The negative impact of amyloid β was seen on five levels of neuronal activities: (1) resting membrane potentials; (2) action potentials; (3) fast inward sodium channels (TTX-sensitive); (4) calcium channels; and (5) outward potassium channels. However, the main ion channel target for amyloid β 1–40 is the TTX-sensitive fast inward sodium channel. This confirms that the deleterious effects of an amyloid β aggregate are upon the fast inward sodium channel, which disables the neurons in terms of generating electrical impulses that are critical for brain and nerve functions.

These results further confirm that low molecular weight peptide aggregates of amyloid β 1–40 monomer have higher potency for inhibiting the fast inward sodium channels.

All of the references cited herein are hereby incorporated in their entireties by reference.

While this invention has been described with an emphasis upon a preferred embodiment, it will be obvious to those of ordinary skill in the art that variations in the preferred composition and method may be used and that it is intended that the invention may be practiced otherwise than as specifically described herein. Accordingly, this invention includes all modifications encompassed within the spirit and scope of the invention as defined by the following claims.

What is claimed is:

1. A method for identifying compounds that modulate the interaction of amyloid β or its aggregates with a voltage-gated sodium channel, said method comprising:
   (a) obtaining a cell that comprises said voltage-gated sodium channel;
   (b) contacting said sodium channel with amyloid β or its aggregates in the presence and absence of a test compound; and
   (c) determining the activity of said sodium channel in the presence of said test compound as compared with in the absence by measuring the voltage-gated fast inward sodium current within from about 0 to about 30 minutes after said contacting, wherein a test compound that impacts activity is considered a modulator of the interaction of amyloid β or its aggregates with said sodium channel.

2. The method of claim 1, wherein said cell is a neuronal cell.

3. The method of claim 1, wherein said cell is a non-neuronal cell.

* * * * *